US009434926B1

(12) United States Patent
Mohapatra et al.

(10) Patent No.: US 9,434,926 B1
(45) Date of Patent: Sep. 6, 2016

(54) GRAPHENE HYDROGEL AND METHODS OF USING THE SAME

(71) Applicants: Subhra Mohapatra, Tampa, FL (US); Chunyan Wang, Tampa, FL (US)

(72) Inventors: Subhra Mohapatra, Tampa, FL (US); Chunyan Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/627,671

(22) Filed: Feb. 20, 2015

Related U.S. Application Data

(63) Continuation-in-part of application No. 13/775,560, filed on Feb. 25, 2013.

(60) Provisional application No. 61/602,352, filed on Feb. 23, 2012, provisional application No. 61/602,378, filed on Feb. 23, 2012, provisional application No. 61/942,556, filed on Feb. 20, 2014.

(51) Int. Cl.
| | |
|---|---|
| A01N 63/00 | (2006.01) |
| A01N 65/00 | (2009.01) |
| C12N 5/00 | (2006.01) |
| C12N 5/02 | (2006.01) |
| C12N 5/0775 | (2010.01) |
| A61K 35/28 | (2015.01) |
| A61K 9/06 | (2006.01) |
| A61K 47/02 | (2006.01) |
| A61K 47/36 | (2006.01) |
| A61K 47/14 | (2006.01) |

(52) U.S. Cl.
CPC ............... *C12N 5/0663* (2013.01); *A61K 9/06* (2013.01); *A61K 35/28* (2013.01); *A61K 47/02* (2013.01); *A61K 47/14* (2013.01); *A61K 47/36* (2013.01); *C12N 2501/00* (2013.01); *C12N 2533/30* (2013.01); *C12N 2533/72* (2013.01)

(58) Field of Classification Search
None
See application file for complete search history.

(56) References Cited

U.S. PATENT DOCUMENTS 5,736,396 A * 4/1998 Bruder ............... A61K 38/1825
424/93.7

OTHER PUBLICATIONS

Ma et al., Carb. Polymers, 79:620-627 (2010).*
Oswald et al., Stem Cells, 22:377-384 (2004).*
Klokkevold et al., Periodontol., 67:1170-1175 (1996).*
Kalbacova et al., Carbon, 48:4323-4329 (2010).*
Vitale-Brovarone et al., Acta Biomaterialia 3:199-208 (2007).*
Alhadlaq et al., Tiss. Eng., 11(3/4):556-566 (2005).*
Lin et al., Tiss. Eng., 14(5):571-581 (2008).*
Mackay et al., Tiss. Eng., 4(4):415-428 (1998).*
Mincheva et al., e-Polymers. 58:1-11 (2004).*
Park et al., J. Cranio-Maxillofacial Surg., 33:50-54 (2005).*
Tuan Thesis (2009).*
Alvarez-Lorenzo, et al., "Light-Sensitive Intelligent Drug Delivery Systems", Photochemistry and Photobiology, vol. 85, pp. 848-860, 2009.

(Continued)

*Primary Examiner* — Thomas J Visone
(74) *Attorney, Agent, or Firm* — Thomas | Horstemeyer, LLP

(57) ABSTRACT

Provided herein are hydrogel compositions containing graphene, chitosan, a polyethylene (glycol) diacrylate (PEGDA). The hydrogel can optionally contain an N-isopropylacrylamide (NIPAM) (TPCG hydrogel). Also provided are methods for differentiating a cell on the hydrogels described herein. Further provided herein are methods for delivering a compound via the hydrogels described herein.

21 Claims, 39 Drawing Sheets

(56) References Cited

OTHER PUBLICATIONS

Bao HQ, et al., "Chitosan-Functionalized Graphene Oxide as a Nanocarrier for Drug and Gene Delivery", Small, vol. 7, pp. 1569-1578, (2011).
Yunqiang Chen, et al, "Graphene oxide—chitosan composite hydrogels as broad-spectrum adsorbents for water purification", J. Mater. Chem A., vol. 1, pp. 1992-2001 (2013).
D. Dapan, et al., "Structure-process-property relationship of the polar graphene oxide-mediated cellular response and stimulated growth of osteoblasts on hybrid chitosan network structure nanocomposite scaffolds", Acta Biomaterialia, vol. 7, pp. 3432-3445 (2011).
Hailong Fan, et al., "Fabrication, Mechanical Properties, and Biocompatibility of Graphene-Reinforced Chitosan Composites", Biomacromolecules, vol. 11, pp. 2345-2351 (2010).
Donglin Han, et al., "Preparation of chitosan/graphene oxide composite film with enhanced mechanical strength in the wet state", Carbohydrate Polymers, vol. 83, pp. 653-658 (2011).
S. Ifuku, et al., "Thermoresponsive chitosan/N-isopropylacrylamide copolymer through atom transfer radical polymerization", International Journal of Biological Macromolecules, vol. 52 pp. 14-19 (2013) Note the earliest available of this publication was Oct. 17, 2012.
Rajendra Kurapati, et al., "Near-infrared light-responsive graphene oxide composite multilayer capsules: a novel route for remote controlled drug delivery", ChemComm, vol. 49, pp. 734-736 (2013).
HN Lim, et al., "Fabrication and characterization of graphene hydrogel via hydrothermal approach as a scaffold for preliminary study of cell growth", International Journal of Nanomedicine, vol. 16, pp. 1817-1823 (2011).
Lv W., et al., "Temperature- and redox-directed multiple self assembly of poly(N-isopropylacrylamide) grafted dextran nanogels", Macromol Rapid Comm., vol. 32, pp. 1101-1107 (2011).
Jiyang Liu, et al., "MultiplepH-responsivegraphenecompositesbynon-covalent modificationwithchitosan", Talanta, vol. 101, pp. 151-156 (2012).
Prakash Rai, et al., "Development and Applications of Photo-triggered Theranostic Agents", Adv Drug Deliv Rev., vol. 62, pp. 1094-1124 (2010).
Joshua T. Robinson, et al., "Ultrasmall Reduced Graphene Oxide with High Near-Infrared Absorbance for Photothermal Therapy", Journal of the American Chemical Society, vol. 133, pp. 6825-6831 (2011).
Muhammad J.A. Shiddiky, et al., "An electrochemical immunosensor to minimize the nonspecific adsorption and to improve sensitivity of protein assays in human serum", Biosensors and Biolelectronics, vol. 38, pp. 132-137 (2012).
Spizzirri, et al., "Temperature-sensitive hydrogels by graft polymerization of chitosan and N-isopropylacrylamide for drug release", (Abstract only) Pharm Dev Technol. Dec. 27, 2011.
Lin Sun, et al., "NIR-Responsive and Lectin-Binding Doxorubicin-Loaded Nanomedicine from Janus-Type Dendritic PAMAM Amphiphiles", Biomacromoledcules, vol. 13, pp. 3581-3591, Sep. 27, 2012, e-published Oct. 9, 2012.
Brian P. Timko, et al., "Remotely Triggerable Drug Delivery Systems", Advanced Materials, vol. 22, pp. 4925-4943 (2010).
Brian P. Timko, et al., "Materials to Clinical Devices: Technologies for Remotely Triggered Drug Delivery", Clinical Therapeutics, vol. 34, pp. 11S, pp. S25-S35 (2012).
Changzheng Wu, et al., "Large-area graphene realizing ultrasensitive photothermal actuator with high transparency: new prototype robotic motions under infrared-light stimuli", Journal of Materials Chemistry, vol. 21, pp. 18584-18591 (2011).
Azami M, Moosavifar MJ, Baheiraei N, Mortarzadeh F, Ai J. Preparation of a biomimetic nanocomposite scaffold for bone tissue engineering via mineralization of gelatin hydrogel and study of mineral transformation in simulated body fluid. Journal of Biomedical Materials Research Part A. 2012;100A:1347-55.
Bahney CS, Hsu CW, Yoo JU, West JL, Johnstone B. A bioresponsive hydrogel tuned to chondrogenesis of human mesenchymal stem cells. Faseb Journal. 2011;25:1486-96.
Bhardwaj N, Kundu SC. Chondrogenic differentiation of rat MSCs on porous scaffolds of silk fibroin/chitosan blends. Biomaterials. 2012;33:2848-57.
Blakney AK, Swartzlander MD, Bryant SJ. The effects of substrate stiffness on the in vitro activation of macrophages and in vivo host response to poly(ethylene glycol)-based hydrogels. Journal of Biomedical Materials Research Part A. 2012;100A:1375-86.
Brighton CT, Krebs AG. Oxygen-Tension of Healing Fractures in Rabbit. Journal of Bone and Joint Surgery—American Volume. 1972;A 54:323-&.
Callahan LAS, Ganios AM, McBurney DL, Dilisio MF, Weiner SD, Horton WE, et al. ECM Production of Primary Human and Bovine Chondrocytes in Hybrid PEG Hydrogels Containing Type I Collagen and Hyaluronic Acid. Biomacromolecules. 2012;13:1625-31.
Feng L, Zhang S, Liu Z. Graphene based gene transfection. Nanoscale. 2011;3:1252-7.
Fernandez MS, Arias JI, Martinez MJ, Saenz L, Neira-Carrillo A, Yazdani-Pedram M, et al. Evaluation of a multilayered chitosan-hydroxy-apatite porous composite enriched with fibronectin or an in vitro-generated bone-like extracellular matrix on proliferation and diferentiation of osteoblasts. Journal of Tissue Engineering and Regenerative Medicine. 2012;6:497-504.
Freier T, Koh HS, Kazazian K, Shoichet MS. Controlling cell adhesion and degradation of chitosan films by N-acetylation. Biomaterials. 2005;26:5872-8.
I. Gorelikov, L. M. Field, E. Kumacheva, 2004 Hybrid Microgels Photoresponsive in the Near-Infrared Spectral Range. Journal of the American Chemical Society, 126, 15938 0002-7863.
Grayson, A.C.R., et al., "Multi-pulse drug delivery from a resorbable polymeric microchip device" Nature Materials (2003) 2, 767.
He XZ, Ma JY, Jabbari E. Effect of Grafting RGD and BMP-2 Protein-Derived Peptides to a Hydrogel Substrate on Osteogenic Differentiation of Marrow Stromal Cells. Langmuir. 2008;24:12508-16.
Heppenstall RB, Grislis G, Hunt TK. Tissue Gas Tensions and Oxygen-Consumption in Healing Bone Defects. Clinical Orthopaedics and Related Research. 1975:357-65.
Hoare, T., et al. "A magnetically-triggered composite membrane for on-demand drug delivery", Nano Lett.,9, 3651-57, (2009).
Hong, Y.; , et al., "Covalently crosslinked chitosan hydrogel: Properties of in vitro degradation and chondrocyte encapsulation", Acta Biomaterialia, vol. 3, Issue 1, Jan. 2007, pp. 23-31.
Huang Y, Zeng M, Ren J, Wang J, Fan L, Xu Q. Preparation and swelling properties of graphene oxide/poly(acrylic acid-co-acrylamide) super-absorbent hydrogel nanocomposites. Colloids and Surfaces a—Physicochemical and Engineering Aspects. 2012;401:97-106.
Kang, H.Z.& Trondoli, A.C.& Zhu, G.Z. et al., "Near-infrared light-responsive core-shell nanogels for targeted drug delivery", ACS Nano, vol. 5, 6, 2011, p. 5094-5099.
Kanichai M, Ferguson D, Prendergast PJ, Campbell VA. Hypoxia promotes chondrogenesis in rat mesenchymal stem cells: A role for AKT and hypoxia-inducible factor (HIF)-1 alpha. Journal of Cellular Physiology. 2008;216:708-15.
Khurma, J.R.& Nand, A.V., "Temperature and pH sensitive hydrogels composed of chitosan and poly(ethylene glycol)", Polymer Bulletin, vol. 59, 2008, p. 805-812.
Koay EJ, Athanasiou KA. Hypoxic chondrogenic differentiation of human embryonic stem cells enhances cartilage protein synthesis and biomechanical functionality. Osteoarthritis and Cartilage. 2008;16:1450-6.
Lee WC, Lim C, Shi H, Tang LAL, Wang Y, Lim CT, et al. Origin of Enhanced Stem Cell Growth and Differentiation on Graphene and Graphene Oxide. Acs Nano. 2011;5:7334-41.
Li WY, et al., "Gold nanocages covered with thermally-responsive polymers for controlled release by high-intensity focused ultrasound. Nanoscale", 2011;3:1724-1730. doi: 10.1039/c0nr00932f.
Lo C-W, Zhu D, Jiang H. An infrared-light responsive graphene-oxide incorporated poly(N-isopropylacrylamide) hydrogel nanocomposite. Soft Matter. 2011;7:5604-9.

(56) References Cited

OTHER PUBLICATIONS

Lu J, Choi E, Tamanoi F, Zink, "Light-Activated Nanoimpeller-Controlled Drug Release in Cancer Cells" Jl. Small., 2008;4:421-426.

Malladi P, Xu Y, Chiou M, Giaccia AJ, Longaker MT. Effect of reduced oxygen tension on chondrogenesis and osteogenesis in adipose-derived mesenchymal cells. American Journal of Physiology—Cell Physiology. 2006;290: C1139-C45.

Z. M. Markovic, L. M. Harhaji-Trajkovic, B. M. Todorovic-Markovic, D. P. Kepić, K. M. Arsikin, S. P. Jovanović, A. C. Pantovic, M. D. Dramićanin, and V. S. Trajkovic, "In vitro comparison of the photothermal anticancer activity of graphene nanoparticles and carbon nanotubes," Biomaterials32(4), 1121-1129 (2011).

Rana VK, Choi MC, Kong JY, Kim GY, Kim MJ, Kim SH, et al. Synthesis and Drug-Delivery Behavior of Chitosan-Functionalized Graphene Oxide Hybrid Nanosheets. Macromolecular Materials and Engineering. 2011;296:131-40.

Motoi Oishi, et al., "Endosomal release and intracellular delivery of anticancer drugs using pH-sensitive PEGylated nanogels", J. Mater. Chem., 2007,17, 3720-3725.

Panyukhin NV, Vishnyakova KS, Yegorov YE. Influence of Partial Oxygen Pressure on Survival, Proliferation, and Differentiation of Mesenchymal Stem Cells from Mouse Bone Marrow. Biologicheskie Membrany. 2008;25:352-9.

Potier E, Ferreira E, Andriamanalijaona R, Pujol J-P, Oudina K, Logeart-Avramoglou D, et al. Hypoxia affects mesenchymal stromal cell osteogenic differentiation and angiogenic factor expression. Bone. 2007;40:1078-87.

\* cited by examiner

| Dexamethasone Absorption | | |
|---|---|---|
| | Mean (μg/mg) | STDEV |
| P | 7.47 | 0.62 |
| PC | 8.78 | 0.25 |
| PG | 8.34 | 0.62 |
| PCG | 10.52 | 0.25 |

FIG. 16A

| Ascorbic Acid Absorption | | |
|---|---|---|
| | Mean (μg/mg) | STDEV |
| P | 0.393 | 0.080 |
| PC | 0.521 | 0.057 |
| PG | 0.535 | 0.068 |
| PCG | 0.690 | 0.089 |

FIG. 16B

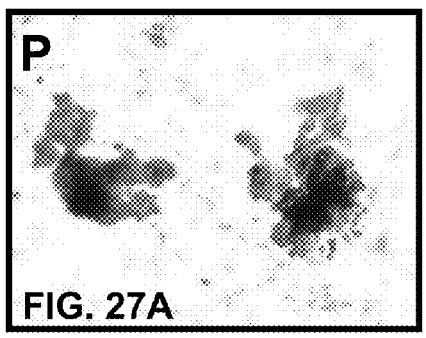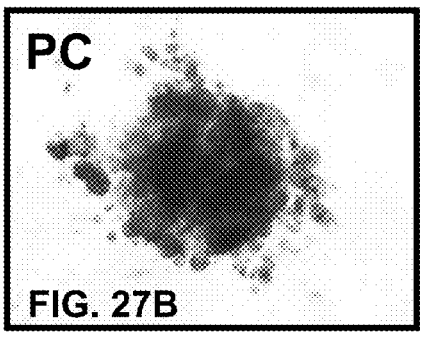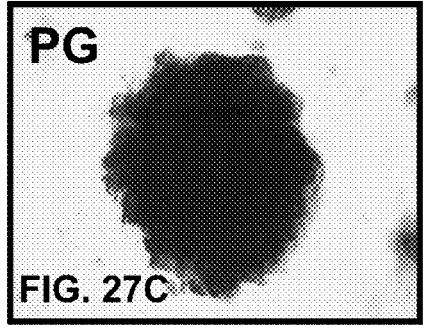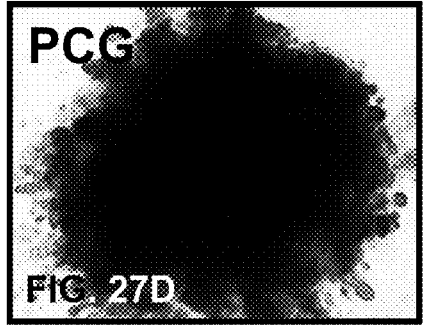
FIGS. 27A-D

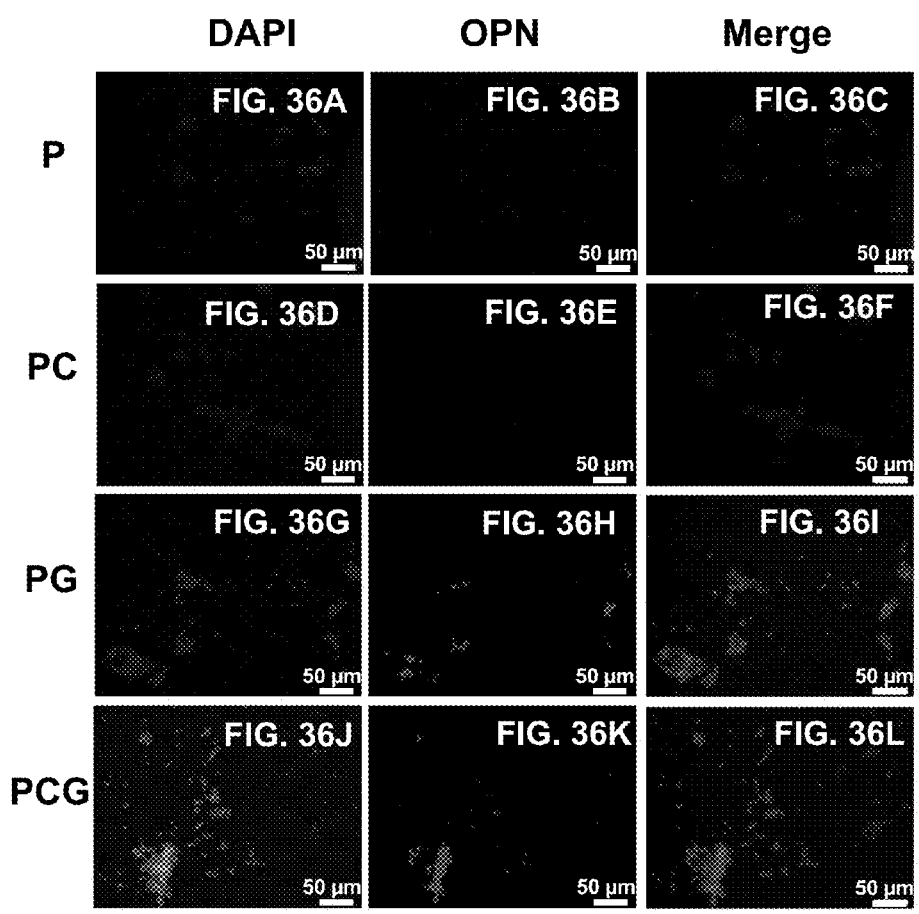
FIGS. 36A-L

GRAPHENE HYDROGEL AND METHODS OF USING THE SAME

CROSS-REFERENCE TO RELATED APPLICATIONS

This application is a continuation-in-part of U.S. application Ser. No. 13/775,560, having the title "Graphene Hydrogel and Methods for Using the Same," filed on Feb. 23, 2013, by Mohapatra et al., which claims the benefit of U.S. Application Ser. No. 61/602,352, filed on Feb. 23, 2012, and U.S. Application Ser. No. 61/602,378, filed on Feb. 23, 2012, which are all incorporated by reference in their entirety. This application also claims the benefit of U.S. Application Ser. No. 61/942,556, having the title "Enhancing Differentiation of Bone Marrow-Derived Mesenchymal Stem Cells in 3-D PEG-Chitosan-Graphene Hydrogels," filed on Feb. 20, 2014, by Mohapatra et al, which is incorporated by reference in its entirety.

STATEMENT REGARDING FEDERALLY SPONSORED RESEARCH OR DEVELOPMENT

This invention was made with government support under Grant Numbers R01 CA152005 and R41 CA139785 awarded by the National Institutes of Health. The government has certain rights in the invention.

BACKGROUND

Cell-based therapies, particularly those utilizing mesenchymal stem cells (MSCs) have potential for tissue regeneration and restoration. However, the full potential of these cell-based therapies has not been realized due to inadequate performance of the cells in vitro, ex vivo, and after transplantation. As such, there exists a long-felt, yet unmet need to improve the performance of cells for use in cell-based therapies so that their full potential can be realized.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 11B) absorbance at 650 nm of TPCG at various temperatures, insert shows the phase transition during temperature change; and (FIG. 11C) absorbance at 650 nm of TPCG after multiple heating/cooling steps.

(FIG. 13B) in vitro drug-release profiles from DOX-TPCG at pH 5.1 (♦) or pH 7.4 (■).

FIGS. 16A and 16B demonstrate the mean dexamethasone (FIG. 16A) or ascorbic acid (FIG. 16B) absorption potential in PCG and different control hydrogels (P, PC, and PG).

FIGS. 27A-27D demonstrate alcian blue staining of glycosaminoglycans (GAGs) present in aggrecan of BM-MSCs encapsulated in different hydrogels (P, FIG. 27A; PC, FIG. 27B; PG, FIG. 27C; or PCG, FIG. 27D) after about 7 days induction in chondrogenic differentiation medium.

FIGS. 36A-36L demonstrates immunostaining for OPN in BM-MSCs cultured on P (FIGS. 36A-36C), PC (FIGS. 36D-36F), PG (FIGS. 36G-36I) or PCG (FIGS. 36J-36L) hydrogels. After about four days in culture without osteogenic induction, BM-MSCs were fixed, counter-stained for OPN (Alexa Fluor 594, red) using an OPN antibody (FIGS. 36A, 36D, 36G, and 36J) and DAPI staining for nuclear localization (blue) (FIGS. 36B, 36E, 36H, and 36K). The merged images are shown in FIGS. 36C, 36F, 36I, and 36L.

(FIGS. 38G-38I) or PCG (FIGS. 38J-38L) hydrogels after about 7 days of treatment with osteogenic differentiation medium. After about 7 days of treatment, cells were stained with DAPI (blue) (FIGS. 38A, 38D, 38G, and 38J) or OPN antibody (red) (FIGS. 38B, 38E, 38H, and 38K). The merged images are shown in FIGS. 38C, 38F, 38I, and 38L.

DETAILED DESCRIPTION

Figure 1A:
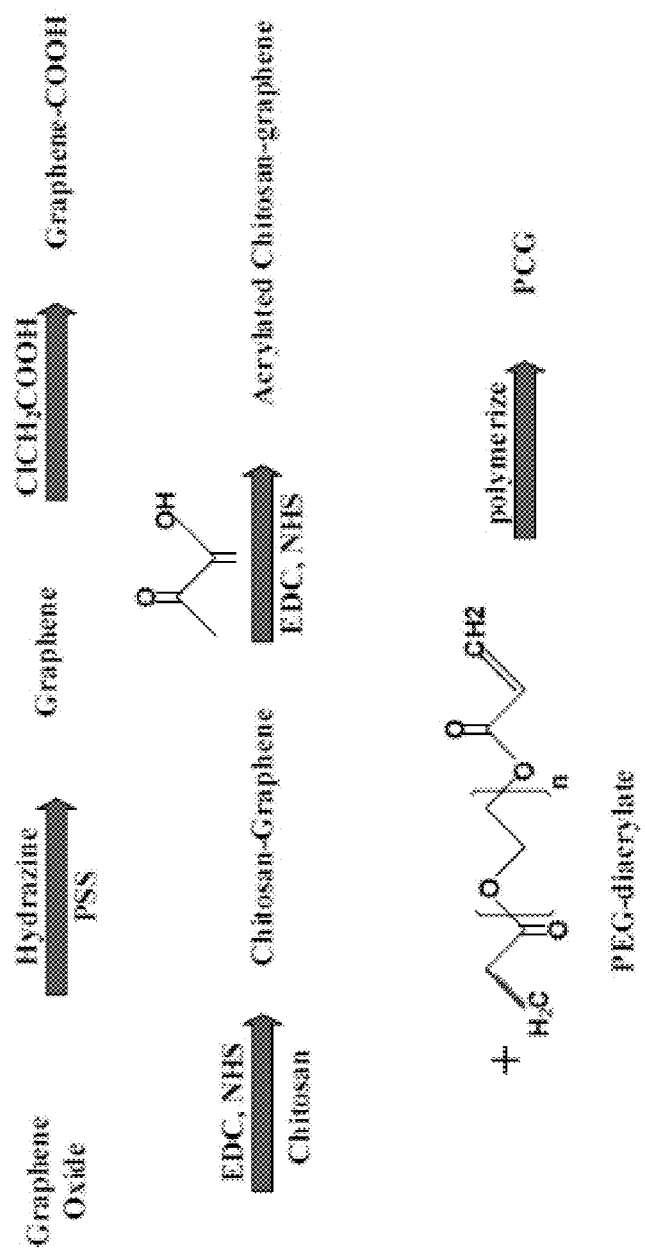
FIGS. 1A-1B show a schematic of PCG hydrogel synthesis.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

DEFINITIONS

As used in the specification and claims, the singular form "a," "an," and "the" include plural references unless the context clearly dictates otherwise. For example, the term "a cell" includes a plurality of cells, including mixtures thereof.

As used herein, the term "adipocyte" refers to a cell type also known as a lipocyte or fat cell. Adipocytes are the cells that primarily compose adipose tissue, specialized in storing energy as fat.

As used herein, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, the terms "cancer," "cancer cells," "neoplastic cells," "neoplasia," "tumor," and "tumor cells" (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor.

As used herein, the terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

As used herein, the term "chondrocyte" refers to a differentiated cell or chondrocyte progenitor cell normally found in healthy cartilage. Chondrocytes produce and maintain the cartilaginous matrix, which consists mainly of collagen and proteoglycans.

As used herein, "composition" is intended to mean a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of,"

when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, a "control" is an alternative subject or sample used in an experiment for comparison purpose. A control can be "positive" or "negative."

As used herein, the term "differentiation" refers herein to the process by which a less specialized cell becomes a more specialized cell type.

As used herein, "effective amount" is an amount sufficient to effect beneficial or desired results. An effective amount can be administered in one or more administrations, applications or dosages.

As used herein, the term "isolated" means separated from constituents, cellular and otherwise, in which the polynucleotide, peptide, polypeptide, protein, antibody, or fragments thereof are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, or antibody, or fragments thereof, does not require "isolation" to distinguish it from its naturally occurring counterpart. In addition, a "concentrated," "separated," or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, or antibody, or fragments thereof, which differs from the naturally occurring counterpart in its primary sequence or, for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

As used herein and for purposes of treatment, "mammal" refers to any animal classified as a mammal, including human, domestic and farm animals, nonhuman primates, and zoo, sports, or pet animals, such as dogs, horses, cats, cows, etc.

As used herein, the term "mesenchymal stem cell," or "MSC," refers to a multipotent stromal cell that can differentiate into a variety of cell types including osteoblasts, chondrocytes, and adipocytes. A cell can be classified as an MSC if it shows plastic adherent properties under normal culture conditions and has a fibroblast-like morphology. In some embodiments, an MSC expresses on the surface CD73, CD90 and CD105, while lacking the expression of CD11b, CD14, CD19, CD34, CD45, CD79a and HLA-DR surface markers.

As used herein, a "mesenchymal stem cell product" refers to a differentiated cell such as an osteoblast, chondrocyte, or adipocyte or a composition produced by an osteoblast, chondrocyte, or adipocyte.

As used herein, the term "osteoblast" refers to a differentiated cell or osteoblast progenitor cell that is normally located in the deeper layer of periosteum and the bone marrow that generates bone tissue. In some embodiments, an osteoblast expresses a range of genetic markers including Osterix, Col1, BSP, M-CSF, ALP, osteocalcin, osteopontin, and osteonectin.

As used herein, the term "osteocyte" refers to a star shaped cell that is most commonly found in mature bone. Osteocytes are cells that contain a nucleus and a thin ring piece of cytoplasm. When osteoblasts become trapped in the matrix that they secrete, they become osteocytes.

As used herein, the term "particulate" refers to powders, granular substances, and the like.

A "pharmaceutical composition" is intended to include the combination of an active agent with a carrier, inert or active, making the composition suitable for diagnostic or therapeutic use in vitro, in vivo, or ex vivo.

As used herein, the term "pharmaceutically acceptable carrier" encompasses any of the standard pharmaceutical carriers, such as a phosphate buffered saline solution, water, emulsions, such as an oil/water or water/oil emulsion, and various types of wetting agents. The compositions also can include stabilizers and preservatives. For examples of carriers, stabilizers, and adjuvants, see Martin, REMINGTON'S PHARM. SCI., 15th Ed. (Mack Publ. Co., Easton (1975)).

As used herein, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, the term "pharmaceutically acceptable salts" refers to any acid or base addition salt whose counterions are non-toxic to the subject to which they are administered in pharmaceutical doses of the salts. Specific examples of pharmaceutically acceptable salts are provided below.

As used herein, the terms "pharmaceutically effective amount," "therapeutically effective amount," or "therapeutically effective dose" refer to the amount of a compound such as a mesenchymal stem cell product that will elicit the biological or medical response of a tissue, system, animal, or human that is being sought by the researcher, veterinarian, medical doctor or other clinician.

As used herein, the terms "prevent," "preventing," "prevention," and grammatical variations thereof as used herein refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

As used herein, "subject," "individual," or "patient," used interchangeably herein, refers to a vertebrate, preferably a mammal, more preferably a human. Mammals include, but are not limited to, murines, simians, humans, farm animals, sport animals, and pets. The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool.

As used herein, the terms "pharmaceutically effective amount," "therapeutically effective amount," or "therapeutically effective dose" refer to the amount of a compound such as a mesenchymal stem cell product that will elicit the biological or medical response of a tissue, system, animal, or human that is being sought by the researcher, veterinarian, medical doctor or other clinician.

As used herein, the term "therapeutically effective amount" includes that amount of a compound such as a mesenchymal stem cell product that, when administered, is sufficient to prevent development of, or alleviate to some extent, one or more of the symptoms of the condition or disorder being treated. The therapeutically effective amount will vary depending on the compound such as a mesenchymal stem cell product, the disorder or conditions and their severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a mesenchymal stem cell product includes an amount that is sufficient to increase healing of a bone fracture or tissue regeneration.

As used herein, the terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

As used herein, "multipotent" refers to the ability of a cell to differentiate into other cell types, but the ability is limited in the number and type of other cell types as compared to pluripotent cells. A cell that has this ability is referred to as a "multipotent cell" or "multipotent stem cell." A multipotent cell is les plastic than a pluripotent or totipotent cell.

As used herein, "pluripotent" refers to the ability of a cell to differentiate into all cell types but they cannot give rise to an entire organism.

As used herein, "totipotent" refers to the ability of a cell to differentiate into any type of cell in the organism and can give rise to an entire organism. A cell that has this ability is referred to as a "pluripotent cell" or "pluripotent stem cell."

As used herein, "stem cell" refers to a cell that have the ability to divide for indefinite periods of time in culture and to differentiate into one or more other cell types.

As used herein, "induced pluripotent stem cells" is a pluripotent cell derived from reprogramming an adult or terminally differentiated cell.

As used herein, "adult stem cell" refers to a multipotent stem cell present in differentiated adult tissue.

Discussion

Regenerative medicine is a promising filed that focuses on the repair or replacement of damaged tissues and organs in the body. Bone marrow-derived mesenchymal stem cells (BM-MSCs) can self-renew and are multipotent. Typically, BM-MSCs are isolated and cultured as a monolayer on a traditional flat culture plate. When cultured as a monolayer, BM-MSCs have a low proliferation rate and a non-specific differentiation capacity, which limits their use in therapeutic purposes. With that said, described herein are compositions and methods of differentiating cells, including MSCs, in/on three-dimensional polyethylene (glycol) diacrylate (PEGDA)-chitosan-graphene hydrogel scaffolds. The compositions and methods described herein can increase differentiation efficiency of the cells, which can improve the efficacy of cell therapies and regenerative tissue techniques.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

PEGDA-Chitosan-Graphene Hydrogels

A hydrogel is a network of polymer chains that are hydrophilic, sometimes found as a colloidal gel in which water is the dispersion medium. Hydrogels are highly absorbent (they can contain over 99.9% water) natural or synthetic polymers. Hydrogels also possess a degree of flexibility very similar to natural tissue due to their significant water content.

Hydrogels are used in a multitude of applications. Hydrogels are used in products as diverse as disposable diapers, contact lenses, EEG and ECG medical electrodes, and water gel explosives. Hydrogels are also used in many biotechnology-related applications. For example, hydrogels are used as scaffolds in tissue engineering and hydrogel-coated wells have been used for cell culture. Environmentally sensitive hydrogels have been created that have the ability to sense changes of pH, temperature, or the concentration of a metabolite and release their load as result of such changes. Hydrogels have also been created for sustained-release drug delivery systems. Some hydrogels are responsive to specific molecules, such as glucose or antigens, and can be used as biosensors.

Noninvasive externally-controlled hydrogel drug release systems are attractive since they allow remote, repeatable and reliable switching on or off of drug release based on need. Generally, a noninvasive remote-controlled drug delivery system comprises a drug, an external stimulus, stimulus-sensitive materials, and stimulus-responsive carriers. The external stimulus can be light, a magnetic field, or ultrasound or radio-frequency [Yavuz, M. S. et al., Nature Materials (2009) 8, 935; Sherlock, S. P. et al., Acs Nano (2011) 5, 1505; Lu, J. et al., Small (2008) 4, 421; Hoare, T. et al., Nano Letters (2009) 9, 3651; Thomas, C. R. et al., J. of the American Chemical Society (2010) 132, 10623; Li, W. Y. et al., Nanoscale (2011) 3, 1724; Santini, J. T. et al., Nature (1999) 397, 335; Grayson, A. C. R. et al., Nature Materials (2003) 2, 767].

An NIR light-triggered release system utilizes the photothermal property of a material, which absorbs NIR light and converts it into heat, thereby inducing the drug release from a thermosensitive carrier. Photothermal materials with strong optical absorbance in the NIR include various gold nanostructures (gold nanorods, gold nanocages, hollow gold nanospheres, gold nanoshells), carbon materials (carbon nanotubes, graphene), or conducting polymers that have been extensively studied for photothermal therapy [Markovic, Z. M. et al., Biomaterials (2011) 32, 1121; Yang, K. et al., Nano Letters (2010) 10, 3318; Tian, B. et al., Acs Nano (2011) 5, 7000; Yang, K. et al., Advanced Materials (2012) 24, 1868]. Gold nanoparticles, gold nanorods, and gold nanocages have been studied for the NIR-triggered drug release by incorporation into thermo-responsive materials [Yavuz, M. S. et al., Nature Materials (2009) 8, 935; Li, W. Y. et al., Nanoscale (2011) 3, 1724; Wu, G. H. et al., J. of the American Chemical Society (2008) 130, 8175]. However, none of these delivery systems have been advanced to clinical trials yet.

Two-dimensional graphene has received considerable attention in biomedical applications in the past few years owing to its high mechanical strength, pH sensitivity, photosensitivity and low toxicity [Yang, K. et al., Nano Letters (2010) 10, 3318; Yang, K. et al., Acs Nano (2011) 5, 516; Yang, X. Y. et al., J. of Materials Chemistry (2011) 21, 3448]. Graphene shows higher photothermal sensitivity than carbon nanotubes (CNT) and was shown to be highly effective in photothermal therapy for cancer [Markovic, Z. M. et al., Biomaterials (2011) 32, 1121; Yang, K. et al., Nano Letters (2010) 10, 3318; Tian, B. et al., Acs Nano (2011) 5, 7000; Yang, K. et al., Advanced Materials (2012) 24, 1868]. In addition, the highly efficient photothermal conversion of graphene enabled graphene oxide/pluronic hydrogel to undergo rapid gelation by NIR laser irradiation [Lo, C.-W. et al., Soft Matter (2011) 7, 5604; Sahu, A. et al., Chemical Communications (2012) 48, 5820]. Whether chemically reduced graphene oxide (GRAPHENE) is capable of acting as a photosensitive material for remote-controlled drug delivery has not been investigated yet.

As mentioned above, hydrogels have also been found to be advantageous when used as scaffolds for cell growth and, in particular, for tissue regeneration. Researchers have found that poor results are obtained when growing cells in a monolayer due to the vast differences in the monolayer cell environment and the in vivo cell environment. Cell morphology, extracellular matrix interactions, three-dimensional organization, oxygen tension, and access to extracellular factors all differ greatly between cells found in a monolayer and cells found in vivo.

Recently, three-dimensional cell cultures have emerged as an alternative to a flat layer of cells. Three-dimensional cell cultures are cellular networks organized in three dimensions—an environment that is much more similar to that found in vivo. Three-dimensional cell cultures have been created using tumor spheroids, embryoid bodies, hanging drop cell cultures, fibrous networks and hydrogels.

Hydrogels are an attractive scaffolding material because their mechanical properties can be tailored to mimic those of natural tissues. As scaffolds, hydrogels are used to provide bulk and mechanical constitution to a tissue construct, whether cells are adhered to or suspended within the three dimensional gel framework. When cellular adhesion directly to the gel is favored over suspension within the scaffold, incorporation of various peptide domains into the hydrogel structure can dramatically increase the tendency for cellular attachment. A particularly successful strategy to mediate cellular attachment is the inclusion of the RGD adhesion peptide sequence (arginine-glycine-aspartic acid). Cells that have been shown to favorably bind to RGD include fibroblasts, endothelial cells (ECs), smooth muscle cells (SMCs), osteoblasts, and chondrocytes. RGD in hydrogels, which can be incorporated on the surface or throughout the bulk of the gel, has shown enhanced cellular migration, proliferation, growth, and organization in tissue regeneration applications.

Unlike conventional hydrogels used in cell and tissue culture and engineering, the hydrogels described herein contain graphene, chitosan, a PEGDA, and optionally an N-isopropylacrylamide (NIPAM). The term "PCG hydrogel" is used herein to describe the PEGDA-chitosan-graphene hydrogel. The term "TPCG" is used to describe the NIPAM-PEGDA-chitosan-graphene hydrogel. Unlike conventional gels having embedded graphene nanoparticles, the hydrogels described herein can have uniform dispersion of graphene within the hydrogel. The uniform dispersion can be facilitated by the grafting of the graphene with the positively charged hydrophilic chitosan present in the hydrogel. Also unlike conventional gels having embedded graphene nanoparticles, the hydrogels described herein can have stable physical dispersion of the graphene nanoparticles within the hydrogels. Further, the PCG hydrogels can maintain their dispersion stability and can have substantially no aggregation or precipitation for at least about three to about four months. The hydrogels described herein can be injectable.

PEGDA

PEGDA was chosen as the cross linker since it has been studied extensively in many biomedical applications due to its outstanding physico-chemical and biological properties such as hydrophilicity, biocompatibility, and lack of toxicity [Khurma, J. R. & Nand, A. V. Polymer Bulletin (2008) 59, 805; Blakney, A. K. et al., J. of Biomedical Materials Research Part A (2012) 100A, 1375; Callahan, L. A. S. et al., Biomacromolecules (2012) 13, 1625]. PEGDA can be hydrophilic and can gel in at room temperature in the presence of a photo-initiator and UV light. In one embodiment, the PEGDA has a molecular weight of approximately 3400 Da. The PEDGA can also have a molecular weight of approximately 250 Da, 575 Da, 700 Da, 2,000 Da, or 6,000 Da. The PEGDA can have be about 50% to about 99% acrylated. In some embodiments, the PEGDA is about 95% acrylated.

Graphene

The 2D graphene sheet is a new biocompatible material that has been studied in the areas of controlled drug delivery, gene delivery, cell culture, cell imaging, and biosensors [Lee, W. C. et al., Acs Nano (2011) 5, 7334; Sun, X. et al., Nano Research (2008) 1, 203; Rana, V. K. et al., Macromolecular Materials and Engineering (2011) 296, 131; Bao, H. Q. et al., Small, (2011) 7, 1569; Zhang, L. M. et al., Small, (2010) 6, 537; Feng, L. et al., Nanoscale, (2011) 3, 1252].

The graphene used in the PCG hydrogel can be any graphene that can be covalently bonded to chitosan and PEGDA. In some embodiments, the graphene is functionalized with an oxygenous group such as hydroxyl, epoxide, or carboxyl. In some embodiments, the graphene can be a carboxylic acid functionalized graphene. The carboxylic acid functionalized graphene can be prepared using graphene oxide at a concentration of approximately 0.25 mg/ml, 0.5 mg/ml, 1 mg/ml, 2 mg/ml, or 3 mg/ml.

Chitosan

Chitosan is a linear polysaccharide prepared by partially or fully deacetylating chitin and is the second most abundant natural polymer found in the shells of shrimps, lobsters and crabs [Zakhem, E. et al., Biomaterials (2012) 33, 4810]. Due to its biocompatibility, biodegradability, and unique physicochemical properties, chitosan has been widely studied in biomedical applications [Azami, M. et al., J. of Biomedical Materials Research Part A (2012) 100A, 1347; Fernandez, M. S. et al., J. of Tissue Engineering and Regenerative Medicine (2012) 6, 497]. In some embodiments, the chitosan has a molecular weight of approximately 10 kDa. The chitosan can also have a molecular weight of approximately 5 kDa, 15 kDa, 20 kDa or 30 kDa. The chitosan can be water soluble or water insoluble, and in one embodiment, the chitosan is water soluble and approximately 10 kDa in molecular weight.

Additional Compounds

NIPAM

In some embodiments, the PCG hydrogel additionally contains N-Isopropylacrylamide (NIPAM). Poly(N-isopropylacrylamide) (PNIPAM) undergoes a reversible discontinuous phase transition in water, changing from hydrophilic (swelling) to hydrophobic (shrinking) in response to a temperature change. Accordingly, PCG hydrogels that further incorporate NIPAM are referred to herein as TPCGs (thermosensitive PCGs). While this thermosensitive property of PNIPAM has been utilized in a switchable drug delivery system via incorporation of stimulus-sensitive materials, these prior art nanogels cannot be maintained as stable nanoparticle dispersions without disturbing the thermosensitivity of the hydrogel matrix.

The hydrogels optionally containing NIPAM as described herein can provide advantages over other conventional materials that contain NIPAM. The low critical solution temperature (LCST) of pure PNIPAM gel crosslinked with N,N'-methylenebisacrylamide (BIS) was shown in the prior art to be 32-34° C. [Yavuz, M. S. et al., Nature Materials (2009) 8, 935; Shiotani, A. et al., Langmuir (2007) 23, 4012]. When the temperature was raised above 32° C., the polymer underwent a phase transition to a hydrophobic state, causing the gel to shrink. Thus, using the prior art PNIPAM hydrogel as the thermosensitive carrier for controlled drug release in vivo would result in a drug release state that would always be 'on.' The hydrogels optionally containing NIPAM described herein can remedy the deficiency of the prior art PNIPAM gel by tuning the LCST of PNIPAM with the acrylated chitosan-graphene. In addition, the hydrophilic biocompatible crosslinker PEGDA was used instead in the presently described hydrogels optionally containing NIPAM instead of hydrophobic BIS.

The TPCG hydrogels provided can have a significant reduction in size when temperature changed from 37° C. to 42° C. In accordance with the size change of TPCG upon heating, the turbidity of the TPCG can also demonstrate the thermosensitive response. The TPCG hydrogels described herein can remain swollen (in the 'off' state) at about 37° C., and can shrink (in the 'on' state) above the phase transition temperature of about 37° C.

The TPCG hydrogels described herein can respond to a specific stimulus. The TPCG hydrogels described herein can have a high drug loading capacity. Conventional hydrogels suffer typically have a low drug loading capacity thus limiting their potential for clinical use. [Shiotani, A. et al., Langmuir (2007) 23, 4012; Gorelikov, I. et al., J. of the American Chemical Society (2004) 126, 15938; Kang, H. Z. et al., Acs Nano (2011) 5, 5094]. The hydrogels described herein can have about a 1-26 wt. % drug loading content. In some embodiments, the hydrogel can have about a 26 wt. %-about a 48% dug loading content. In further embodiments the hydrogel can have about a 48% drug loading content.

Pharmaceutical Compounds

The PCG or TPCG hydrogels can optionally contain an effective amount of one or more suitable pharmaceutical compounds. Suitable pharmaceutical compounds include, but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veraliperide, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Cells

The hydrogels described herein can include one or more cells. The cells can be embedded in the hydrogel. The embedded cells can be uniformly dispersed throughout the hydrogel. The embedded cells can have a non-uniform distribution throughout the hydrogel. The cells can be present on a surface of the hydrogel. The cells can be pluripotent cells, multipotent cells, and/or fully or partially differentiated cells, or combinations thereof. The cells can be primary cells, secondary cells, or combinations thereof. The cells can be multipotent stem cells, totipotent stem cells, pluripotent stem cells, induced pluripotent stem cells, adult stem cells, or combinations thereof. The cells can be derived from any tissue in an organism. In some embodiments the cell(s) can be derived from bone marrow. The cells derived from bone marrow can be bone-marrow mesenchymal stem cells, bone marrow stromal cells, or combinations thereof. The cells can be fibroblasts, chondrocytes, adipocytes, osteoblasts, or combinations thereof. The cells can be autologous, allogeneic, xenogeneic, or isogeneic.

Nutrients, Growth Factors, and Other Molecules

The hydrogels described herein can optionally include one or more suitable nutrients. Suitable nutrients include, but are not limited to, carbohydrates, fats, proteins, amino acids, minerals, vitamins, organic acids, Suitable carbohydrates can include, but are not limited to, fructose, glucose, sucrose, ribose, amylose, amylopectin, maltose, lactose, and galactose.

Suitable fats can include, but are not limited to, butyric acid, caproic acid, caprylic acid, capric acid, lauric acid, myristic acid, pentadecanoic acid, palmitic acid, margaric acid, stearic acid, arachidic acid, behenic acid, lignoceric acid, cerotic acid, myristol, mentadecenoic, palmitoyl, heptadecenoic, oleic acid, eicosen, erucic acid, nervonic acid, linoleic acid, alpha-linolenic acid, stearidonic acid, arachidonic acid, timnodonic acid, clupanodonic acid, cervonic acid, omega-3 fatty acid, and omega-6 fatty acid.

Suitable amino acids can include, but are not limited to, arginine, aspartic acid, asparagine, cystine, glutamic acid, glycine, histidine, isoleucine, leucine, lysine, methionine, phenylalanine, proline, serine, threonine, tryptophan, tyrosine, and valine.

Suitable minerals can include, but are not limited to, boron, cobalt, chromium, calcium, copper, chloride, phosphorus, potassium, sodium, fluoride, iodine, iron, magnesium, manganese, molybdenum, selenium, and zinc.

Suitable vitamins can include, but are not limited to, thiamin, riboflavin, niacin, pantothenic acid, vitamin $B_6$ complex (pyridoxine, pyridoxal and pyridoxamine), biotin, ergadenylic acid, folic acid, cyanocobalamin, choline, retinol (vitamin A), ascorbic acid (vitamin C), vitamin D, tocopherol (vitamin E), vitamin K, carotenoid (alpha carotene, beta carotene, cryptoxanthin, lutein, lycopenem and zeaxanthin).

Suitable organic acids can include, but are not limited to, acetic acid, citric acid, lactic acid, malic acid, choline, and taurine.

The hydrogels can contain one or more suitable extracellular matrix components. Suitable extracellular matrix components can include, but are not limited to, proteoglycans such as heparan sulfate, chondroitin sulfate, and keratan sulfate, non-proteoglycan polysaccharides, such as hyaluronic acid, fiber proteins such as collagen and elastin, and fibronectin and laminin.

Suitable growth factors include, but are not limited to, adrenomedullin, angiopoietin, autocrine motility factor, bone morphogenetic proteins, brain-derived neurotrophic factor, epidermal growth factor, glial cell line-derived neurotrophic factor, granulocyte macrophage coloy-stimulating factor, growth differentiation factor-9, healing factor, hepatocyte growth factor, hepatoma-derived growth factor, insulin-like growth factors, keratinocyte growth factors, migration-stimulating factor, myostatin, nerve growth factor, neurotrophines, platelet-derived growth factor, thrombopoietin, transforming growth factor alpha (TGF-alpha), transforming growth factor beta (TGF-beta), tumor necrosis factor-alpha (TNF-alpha), vascular endothelial growth factor, placental growth factor, fetal bovine somatotrophin, IL-1, IL-2, IL-3, IL-4, IL-5, IL-6, IL-7, and renalase.

Methods of Making the PEGDA-Chitosan-Graphene Hydrogels

Conventionally, nanoparticles such as graphene were embedded in gels by polymerization of a mixture of the monomer and nanoparticles [Sershen, S. R. et al., J. of Biomedical Materials Research (2000) 51, 293; Sershen, S. R. et al., Applied Physics B-Lasers and Optics (2001) 73, 379; Wang, C. et al., Advanced Materials (2004) 16, 1074]. However, the physical dispersion of nanoparticles inside the gels was not stable and uniform [Shiotani, A. et al., Langmuir (2007) 23, 4012]. In contrast, the hydrogels described herein can provide a means for stable incorporation of graphene into a gel. More specifically, graphene can be grafted with positively charged hydrophilic chitosan, which can increase the dissolution of nanoparticles and prevent the aggregation [Bao, H. Q. et al., Small (2011) 7, 1569]. Compared to conventional physical mixing, the graphene nanoparticles of the hydrogels described herein can be uniformly dispersed inside the hydrogel via chemical bonds.

Figure 1B:
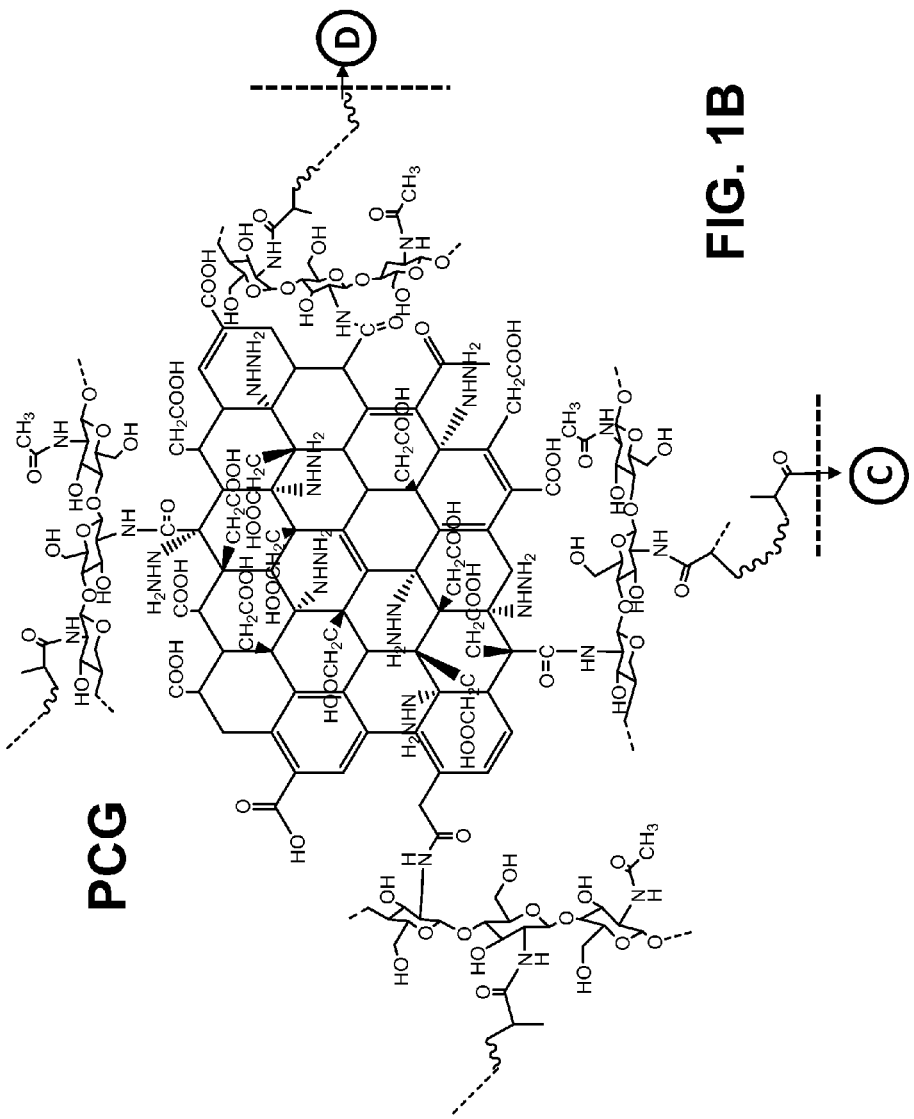

FIGS. 1A-1B shows a scheme that can be used to synthesize the hydrogels described herein. The PCG hydrogel can be synthesized by functionalizing graphene with chitosan. The resulting graphene-chitosan can then be acrylated to form an acrylated chitosan-graphene monomer. The acrylated chitosan-graphene monomer, can then be crosslinked with PEG-diacrylate.

Hydrogels optionally containing NIPAM, the NIPAM can be mixed and with PEGDA and acrylated chistosan-graphene for simultaneous covalent bonding of NIPAM and PEGDA to chitosan-graphene to form a TPCG.

Additional components such as pharmaceutical compounds or compositions can be added to the hydrogels described herein via chemical conjugation, physical entrapment during polymerization, or physical diffusion.

Methods of Using the PEGDA-Chitosan-Graphene Hydrogels

Cell Culture and Tissue Engineering

The hydrogels described herein can provide a three-dimensional cell culture substrate on which cells can be grown and/or differentiated. Cells can be obtained from a subject or cell repository (e.g. ATCC) and seeded on a surface and/or embedded in a hydrogel. Cells can be cultured for an amount of time at a suitable temperature in a suitable culture medium. The culture medium can contain compounds which promote differentiation of the cells (differentiation medium). One of ordinary skill in the art will appreciate that the exact formulation of the cell culture medium is dependent at least on the type of cell and the specific differentiation pathway that is desired. The amount of time can vary from about 1 hour to about 14 days. The cell culture medium can be changed at various intervals during the cell culture period. In some embodiments, the culture medium can be changed from standard cell culture medium (culture medium without differentiation factors) to differentiation medium and vice versa. In some embodiments, the cells, such as stem cells and BM-MSCs, seeded or embedded on the hydrogel differentiate. The cells can differentiate into adipocytes, chondrocytes, and/or osteocytes. In some embodiments, the cells are cultured in media that promotes development of complex tissues, such as cartilage. In some embodiments, the cells are cultured on the hydrogels under mechanical or shear stress from fluid flow.

After a period of time, the cells can be harvested and separated from the hydrogel. The cells can then be delivered to a subject in need thereof via a suitable method, such as injection. In other embodiments, the cells and the hydrogel are harvested and delivered to a subject in need thereof via a suitable method such as injection. The cells and/or the cells/hydrogel can be administered to a subject to treat a disease, condition, or symptom thereof, including, but not limited to, cancer, cardiovascular disease or myocardial infarction (MI), brain or spinal cord injury, stroke, diabetes, cartilage or bone injury, Crohn's disease, or graft versus host disease (GvHD). The terms "treat," "treating," "treatment," and grammatical variations thereof as used herein include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially.

Drug Delivery

The hydrogels described herein can be used to deliver a pharmaceutical compound or composition, nutrient, or other molecule to a subject in need thereof. In some embodiments, the hydrogels can deliver a pharmaceutical compound, nutrient, or other molecule to a subject in need thereof in a thermally inducible manner. In other words, in some embodiments, the hydrogels described herein can serve as a thermally inducible delivery vehicle for a pharmaceutical compound or composition, nutrient, or other molecule to a subject in need thereof. In some embodiments, the TPCG hydrogels described herein can be used to deliver a pharmaceutical compound or composition, nutrient, or other molecule to a subject in need thereof.

Delivery of a pharmaceutical compound or composition, nutrient, or other molecule to a subject in need thereof can occur by diffusion that can occur during the swelling/shrinking process that can occur in the hydrogels. In some embodiments, the swelling/shrinking of the hydrogel can be reversible and thus the hydrogel can have a "switchable" release behavior. The size transition can be in response to heat induced from suitable heat source. Suitable heat sources include, but are not limited to lasers or other light sources that generate absorbable light that can be converted to heat through a photothermal response of the graphene in the hydrogel. In some embodiments, the heat source can be a near infrared-laser. Other suitable heat sources will be instantly appreciated by one of ordinary skill in the art.

Delivery of the drug by the hydrogel can occur when the temperature of the hydrogel is raised by the heat source such that the temperature is raised above the phase change temperature, which causes the hydrogel to shrink and release the pharmaceutical compound or composition, nutrient or other molecule, into the surrounding environment. When the heat source is removed, such as when the light source is turned off, the hydrogel can decrease in temperature to a temperature at or below the phase change temperature causing the hydrogel to swell, which can stop the release of the pharmaceutical compound or composition, nutrient, or other molecule from the hydrogel.

Accordingly, further provided herein is a method for delivering a pharmaceutical compound or composition, nutrient, or other molecule to a cell containing the steps of administering to the cell a TPCG hydrogel and the pharmaceutical composition and subsequently increasing the temperature of the TPCG hydrogel to at or above a TPCG phase change temperature. The TPCG phase change temperature can be approximately 35° C., 36° C., 37° C., 38° C., 39° C., 40° C., 41° C. or 42° C. In one embodiment, the TPCG phase change temperature is approximately 37° C.

The hydrogels described herein can be administered to a subject for treatment of a disease or condition. The hydrogels of the present invention can be administered via any route. Examples of administration routes include oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via implantation. The term "parenteral" includes subcutaneous, intravenous, intramuscular, intra-articular, intra-synovial, intrasternal, intrathecal, intrahepatic, intralesional, and intracranial injections or infusion techniques.

The hydrogels described herein, such as the TPCG gels having a pharmaceutical compound or composition, nutrient, or other molecule can be delivered to a subject in need thereof for treatment of a disease, condition, or symptom thereof including, but not limited to, cancer, cardiovascular disease or myocardial infarction (MI), brain or spinal cord injury, stroke, diabetes, cartilage or bone injury, Crohn's disease, or graft versus host disease (GvHD). The terms "treat," "treating," "treatment," and grammatical variations thereof as used herein include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Preparation and Characterization of a PCG Hydrogel

A PCG hydrogel was prepared based on a chitosan modified graphene and poly(ethylene glycol) (PEG) according to FIGS. 1A-1B. To increase the carboxylic acid groups on the surface of graphene sheets, graphene oxide was first reduced to graphene and then reacted with $ClCH_2COOH$. Chitosan was covalently bonded to graphene via amide bonds by reacting the amine groups of chitosan with the COOH groups of graphene in the presence of EDC and NHS. The chitosan functionalized graphene was further reacted with acrylic acid to form an acrylated chitosan-graphene monomer which was crosslinked with PEGDA to form a PEG-Chitosan-Graphene hydrogel (PEGDA-chitosan-graphene hydrogel).

More specifically, the following materials were used: Graphene oxide 0.5% water solution (Angstron Materials Inc., OH, USA), water soluble chitosan (Mw, 10 kDa) was donated from Transgenex Nanobiotech Inc. Poly (ethylene glycol) diacrylate (PEGDA), Tetramethylethylenediamine (TEMED), Ammonium persulphate (APS), acrylic acid anhydrous, ethyl (dimethylaminopropyl) carbodiimide (EDC), and N-Hydroxysuccinimide (NHS).

To prepare acrylated-Chitosan graphene, graphene-COOH was prepared according to the reported procedure with minor modification. PSS-coated reduced graphene oxide (GO) sheets were prepared by reduction of GO (about 1 mg/mL) in the presence of poly(sodium 4-styrenesulfonate) (PSS) (about 15 mg/mL) and about 1.5 ml hydrazine under refluxing at about 100° C. (Stankovich, S. et al., Nature (2006) 442, 282). After cooling down to about room temperature, NaOH (about 1.2 g) and chloroacetic acid ($ClCH_2COOH$) (about 1.0 g) were added to the GO-PSS solution and sonicated for about 3 hours (Sun, X. et al., Nano Research (2008) 1, 203) to convert the OH groups to COOH via conjugation of acetic acid moieties resulting in graphene-COOH.

Chitosan-graphene was then prepared as follows. About 1 mL graphene-COOH suspension (about 1.28 mg graphene) was activated with EDC (30 mg) and NHS (30 mg) in about 1 mL of water for about 30 minutes and added to water soluble chitosan solution (about 150 mg in about 10 mL water). The reaction was kept for about 3 hours before dialyzing with about 1000 molecular weight cutoff dialysis bag for about 2 days. Finally, acrylated-chitosan-graphene was prepared by adding EDC and NHS activated acrylic acid (about 10 μl) to the chitosan-graphene solution. After reacting for about 3 hours, the solution was purified by dialysis with a dialysis bag having about a 12-14 k molecular weight cuttoff for 2 days. The purified solution was lyophilized.

Acrylated chitosan was prepared by adding EDC and NHS activated acrylic acid (about 10 ul) to 10 ml chitosan solution (150 mg). The purification procedure was the same as the acrylated chitosan-graphene.

Then about 450 μl of 1 mg/mL of acrylated chitosan-graphene solution was added to about 2 mL centrifuge tube with about 956 μl de-ionized water. About 45 μl of about 10 wt % APS and PEG-diacrylate was added to the tube and vortexed to mix well. The solution was purged with argon gas for about 30 seconds. About 4 μl of TEMED was added to the solution and vortexed for about 1 second. About 75 μl of the solution was added to each well of the 96-well plates. The solution was left for about 5 min to form the PEG-chitosan-graphene (PCG) hydrogel.

The PEG hydrogel and Chitosan PEG hydrogel controls were prepared the same way but without acrylated chitosan-graphene solution or with acrylated chitosan instead of the acrylated chitosan-graphene solution. After forming the hydrogel in the wells, 200 μl of deionized water was added to each well to wash the hydrogel about every 2 hours for about one week. Before the cells were plated onto hydrogel, the hydrogel was washed one time with PBS and one time with DMEM and sterilized for about 2 hours with UV light.

Figure 2:
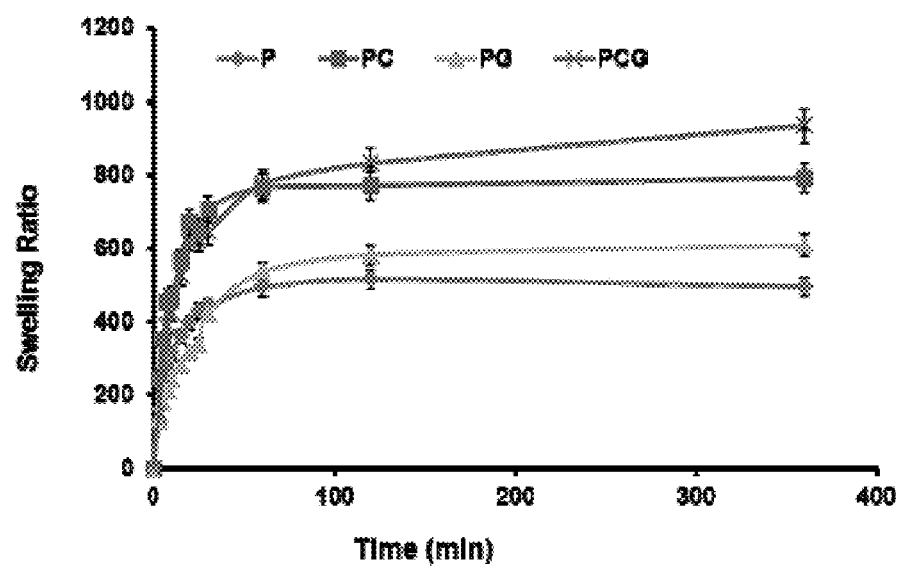
FIG. 2 is a graph showing the swelling kinetics for PEG hydrogel (P), PC hydrogel, PG hydrogel, and PCG hydrogel.
Figure 3:
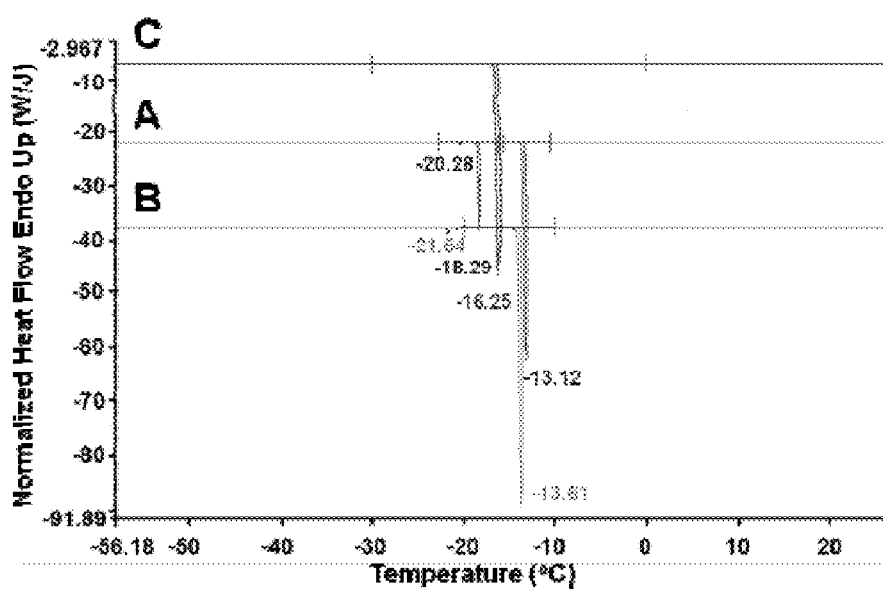
FIG. 3 is a graph showing the DSC cooling curves of (A) PEG hydrogel, (B) PC hydrogel, and (C) PCG hydrogel.

The inner morphology of the hydrogel was examined using scanning electron microscopy (SEM), hydrogel samples were cut to about 10 μm thick and freeze-dried. The morphology of the freeze-dried gels was examined using a Jeol SEM. FIG. 2 shows the cross-section morphology of PEG hydrogel, PEG-chitosan hydrogel and PEG-chitosan-graphene hydrogel. The inner morphology of PEG, chitosan-PEG, and graphene-chitosan-PEG hydrogel shows well defined and interconnected spider net-like structure on the surface of the pores. The microarchitecture of the hydrogel is very similar to the extracellular matrix (ECM). PEG hydrogel and PEG-chitosan hydrogel demonstrate some big pieces of plates between the nets. Compared to the PEG-chitosan hydrogel, the morphology of PEG-chitosan-graphene hydrogel is more net-like and uniformly dispersed. It indicates that the presence of graphene inside the hydrogel could enable the microarchitecture to be more uniform and more porous, which could benefit the nutrient transport.

The swelling rate of PEG hydrogel, PEG-Chitosan hydrogel and PEG-Chitoan-Graphene hydrogel were determined as follows: Hydrogel samples were freeze-dried for about one day and stored in a desiccator at about room temperature. The sorption behavior of hydrogels was monitored by detecting the increase in mass of the samples at different time intervals by a balance. In a typical sorption experiment, a pre-weighed dry gel sheet was immersed in water at 24±1° C. water bath. At prescribed time intervals, the hydrogel was taken out of solution and weighed after wiping off the excess water from the surface with Kimwipe paper (Kimberly Clark Professional). The sorption degree, SD, of hydrogels was defined as follows: SD %=(Wt−Wd)×100/Wd=Mt×100/Wd where Wd is the weight of the dry gel, Wt is the weight of wet hydrogel at each time interval, and Mt is the gain in the weight of the dry gel at time t.

The results of the sorption analyses are shown in FIG. 2. The swelling rate of all three hydrogels was fast at the beginning and then leveled off. The PEG hydrogel achieved equilibrium within 1 hour, but PEG-Chitosan and PEG-Chitosan-Graphene achieved equilibrium within 3.5 hours. Accordingly, it took a longer time to arrive at the swelling equilibrium for PEG-chitosan hydrogel and PEG-Chitosan-graphene hydrogel. The equilibrium swelling degree of PEG-Chitosan hydrogel was higher than PEG hydrogel. The amino groups of the chitosan are hydrophilic, which can attract more water to hydrogel.

The equilibrium swelling degree of PEG-chitosan-graphene hydrogel was greater than chitosan-PEG. It was reported that the swelling capacity of the hydrogel exhibited significant improvement when graphene oxide content inside the P(AA-co-AM) hydrogel increased from 0 to 0.1% (Huang, Y. et al., Colloids and Surfaces a-Physicochemical and Engineering Aspects (2012) 401, 97). The GO/PVA with 0.6% GO among 0.0, 0.2%, 0.4%, 0.6% GO/PVA hydrogel has the highest maximum swelling ratio (Zhang, L. et al. J. of Materials Chemistry (2011) 21, 10399). The hydrogel described in this Example contains approximately 0.08 wt % graphene and demonstrated a trend similar to the reported results. The improvement of swelling capacity of the low graphene containing hydrogel might be due to the high density of hydrophilic groups on the surface of the graphene sheet, the homogenously dispersed graphene sheet influencing the microstructure of polymer network, or some synergetic intermolecular interactions between graphene oxide (GO) sheets and polymer networks for holding water (Huang, Y. et al., Colloids and Surfaces a-Physicochemical and Engineering Aspects (2012) 401, 97).

The crystallization process of water inside the hydrogel is complicated and related to the water content of hydrogel. Water inside of a hydrogel can be classified into non-freezing, freezing bound and free water according to the phase transition, and molecular mobility of the water can be tested by NMR, TGA, FTIR and DSC (Yoshida, H. et al., J. of Thermal Analysis (1993) 40, 483; Wang, C. et al., Biomacromolecules (2008) 9, 561). The non-freezing water forms hydrogen bonds with polymer chains, which are immobilized and show no freezing peak even up to about −100° C. Freezing bound water interacts weakly with polymer molecules and has a melting endotherm below about 0° C. Free water does not take part in hydrogen bonding with polymer chains and behaves similarly with pure water.

Figure 4:
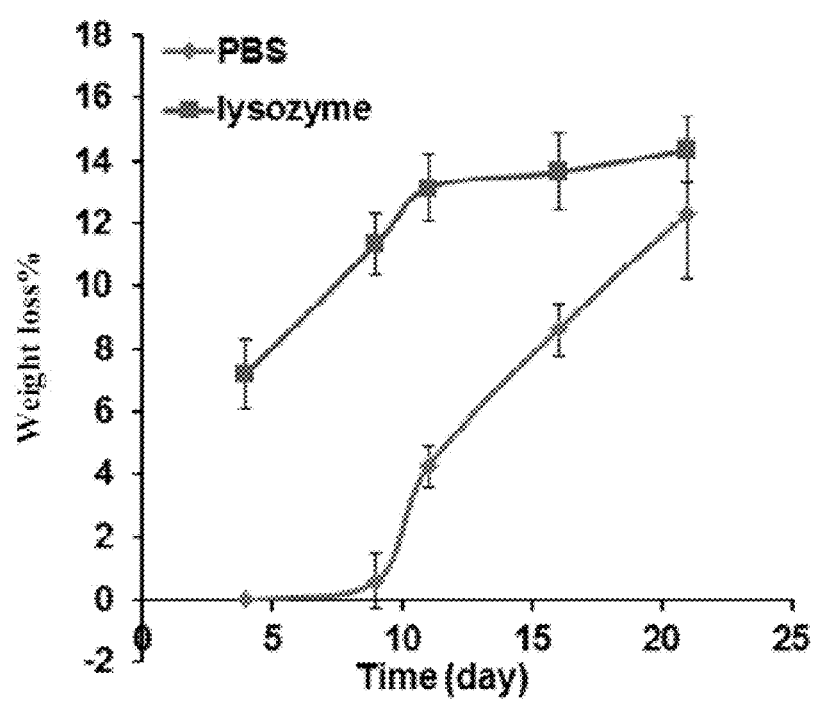
FIG. 4 is a graph showing the degradation degree of PCG hydrogel after 3 weeks of incubation with 0.1 M PBS or 1 mg/ml lysozyme at 37° C.

FIG. 4 shows the schematic DSC cooling curves of the equilibrium swollen PEG hydrogel, PEG-chitosan hydrogel and PEG-chitosan-graphene hydrogel. Three exothermic peaks (sharp big at about −13.12° C., sharp medium at about −18.29° C., small at about −20.28° C.) of crystallization were observed during the cooling process of equilibrium swollen PEG hydrogel. Two exothermic peaks (sharp at about −13.61° C., tiny at about −21.64° C.) were observed on the equilibrium swollen PEG-Chitosan hydrogel cooling curve. However, the PCG hydrogel cooling curve only demonstrated one sharp big peak at about −16.25° C., which was lower than the first peak of PEG or PEG-Chitosan. As the rate of crystallization of freezing bound water is slower than that of free water, the crystallization at about −18.29° C., about −20.28° C., and about −21.64° C. represents the freezing bound water in the form of metastable ice and the crystallization at about −13.12° C. and about −13.61° C. represents the free water in the form of stable hexagonal ice. In equilibrium swollen PCG hydrogel, the crystallization of free water was observed to be delayed and freezing bound water was observed to be early such that they are merged together to form one sharp peak.

In tissue engineering, the regeneration of the tissue is accompanied by the degradation of the supporting matrix for the implanted cells. The degradation rate of matrix can affect the restoration of the tissue: matrix degradation that is too quick could release cells and matrix components, while matrix degradation that is too slow could inhibit matrix production and assembly (Bahney, C. S. et al., Faseb Journal (2011) 25, 1486). Chitosan degrades slowly in vitro in PBS, but degradation rate will be accelerated in the presence of the lysozyme, which is the primary enzyme responsible for in vivo degradation of chitosan through hydrolysis of the glycosidic bonds (Hong, Y. et al., Acta Biomaterialia (2007) 3, 23; Freier, T. et al., Biomaterials (2005) 26, 5872). To mimic the in vivo degradation performance, the degradation kinetics of the PCG hydrogel was examined in the presence of lysozyme under accelerated conditions compared to the PBS (FIG. 4). The degree of degradation was estimated in terms of change of dry weight of the hydrogel. Gels were incubated in about 0.1 M PBS (pH7.4) or about 1 mg/ml lysozyme PBS solution at about 37° C. for the duration of about 21 days. In about 3 days, no degradation was observed in PBS and about 7% loss was observed in lysozyme. In about 9 days, only about 1% weight loss was observed in PBS, but an 11% loss was observed in lysozyme. After about 9 days, the degradation rate increased in PBS but slowed down in lysozyme. The degradation behavior of PCG hydrogel in lysozyme is in accordance with the reported results of a PEG cross-linked chitosan hydrogel film (Tanuma, H. et al., J. of Applied Polymer Science (2009) 114, 1902).

Example 2

Cell Viability and Morphology of Cells Placed on a PCG Hydrogel

The cell morphology of BM-MSCs cultured on a monolayer, PEG hydrogel, a PC hydrogel, a PG, and a PCG hydrogel was investigated with Calcein AM staining (data not shown). The cells cultured on the monolayer form a spindle-shape. The cells were observed to be fine and formed a rounded shape on the four hydrogels. The proliferation rates of BM-MSC on PG and PCG hydrogel decreased compared to PEG and PC hydrogels. Some possible reasons for these observations are as follows: (1) graphene is cytotoxic or (2) BM-MSCs differentiate into other lineages because of the unique properties of the graphene incorporated into the hydrogel. From the EthD-1 staining, it was observed that BM-MSCs on graphene incorporated hydrogel PG and PCG appeared more biocompatible than PEG or PC hydrogel. This suggests that the cytotoxicity of graphene is not the main reason for the lower proliferation rate of BM-MSCs on graphene incorporated hydrogel. The big nodules and connection between nodules was also observed on the PCG hydrogel, which suggests a cell-cell or cell-substrate interaction.

Example 3

Adipogenic Differentiation of Cells Placed on a PCG Hydrogel

Figure 5:
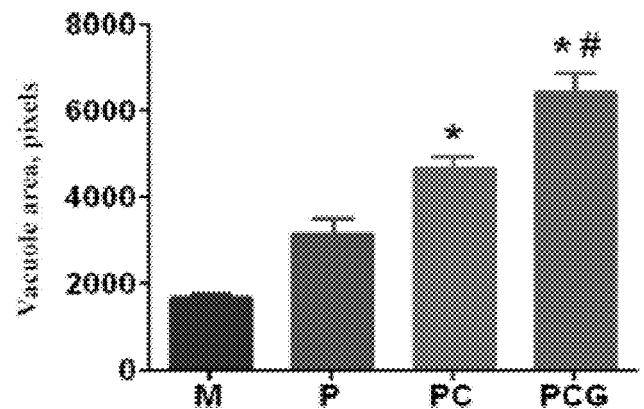
FIG. 5 is a graph showing adipogenesis of BM-MSCs with induction under nomoxia. More vacuoles were found in adipocytes differentiated in PCG hydrogel. The area of fat vacuole per cell was quantified with imageJ after mouse MSCs were cultured overnight on three different hydrogels in a 96-well plate. From the second day, adipocyte differentiating medium was added to the cells under nomoxia. On the seventh day, the cells were stained with Oil red O. M=monolayer, P=PEG hydrogel, PC=PC hydrogel, and PCG=PCG hydrogel. Cells from 4 fields/groups were analyzed. #$p<0.01$; PEG vs Graphene. *$p<0.05$; PC vs PCG.
Figure 6:
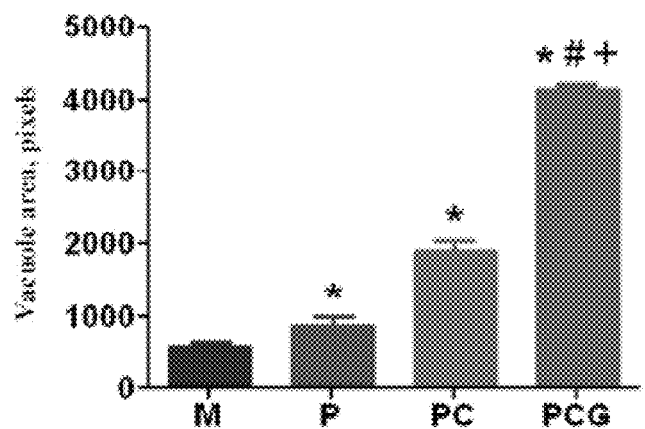
FIG. 6 is a graph showing adipogenesis of BM-MSCs with induction under hypoxia. More vacuoles were found in adipocytes differentiated in PCG hydrogel. Mouse MSCs were cultured overnight on three different hydrogels in a 96-well plate. From the second day, adipocyte differentiating medium was added to the cells under hypoxia. On the seventh day the cells were stained with Oil red O. M=monolayer, P=PEG hydrogel, PC=PC hydrogel, and PCG=PCG hydrogel. Area of fat vacuole per cell was quantified with imageJ. Cells from 4 fields/group were analyzed. #$p<0.01$; PEG vs Graphene. *$p<0.05$; PC vs PCG.

The adipogenic differentiation of MSCs on the hydrogels described herein was determined by specifically staining intra-cytoplasmic lipids with Oil Red O and quantifying these lipids by normalizing the total area of lipid droplets per cell. Without the differentiation medium, no adipogenesis was observed on the hydrogel (data not shown). Compared to a monolayer, cultures on the 3D hydrogel demonstrated intensive staining. Compared to the PEG hydrogel and PEG-chitosan hydrogel, the PCG hydrogel was observed to have the most lipid droplets and exhibited the greatest levels of oil red O staining. See FIG. 5. Accordingly, graphene incorporated into 3D hydrogel was observed to significantly enhanced the adipogenic differentiation instead of inhibiting such differentiation, which is observed with graphene materials in the prior art. These results suggest potential applications of graphene-chitosan-PEG hydrogel for adipose tissue regeneration. FIG. 6 also demonstrates that the PCG hydrogels support adipogenic differentiation of MSCs under hypoxic conditions.

Example 4

Osteogenic Differentiation of Cells Placed on a PCG Hydrogel

Implanting biocompatible and biodegradable hydrogel with BM-MSCs cells is a promising approach for repairing bone fractures. However, the clinical application of this technique is limited by the differentiation gap. In this Example, the influence of the graphene on the osteogenic differentiation of BM-MSCs in a hydrogel was investigated by plating mouse BM-MSCs on PCG hydrogel. The osteogenic differentiation of BM-MSCs was evidenced by the accumulation of calcium or an increase in alkaline phosphatase, which is an early marker of osteogenesis. Without induction under normoxia, the osteogenesis of BM-MSCs was only observed on PCG hydrogel (data not shown). This result indicated that the nanostructure of the graphene and chitosan can induce the osteogenesis of BM-MSC.

Figure 7:
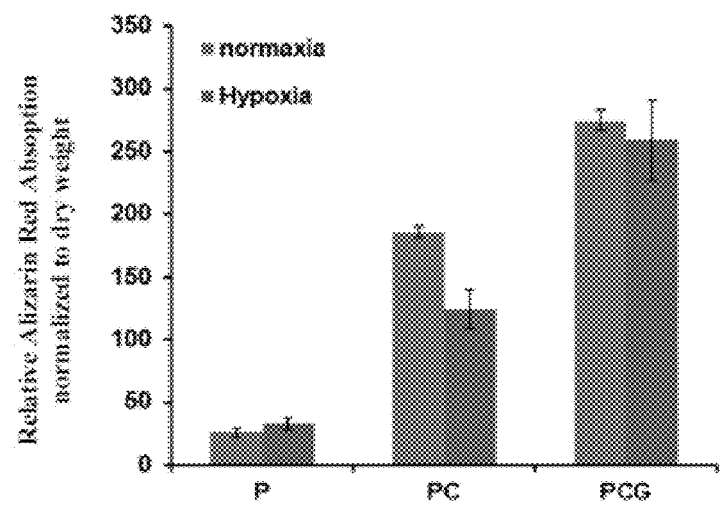
FIG. 7 is a graph showing osteogenesis of BM-MSCs with induction under normoxia and hypoxia. Osteogenic differentiation of BM-MSC was first visualized by staining at normoxia and hypoxia conditions after 7 days of incubation on hydrogels. Alizarin Red quantification was performed by UV-vis absorption and normalized to the dry weight of hydrogel and cells. M=monolayer, P=PEG hydrogel, PC=PC hydrogel, and PCG=PCG hydrogel.

After 7 days of osteogenic induction, the extent of mineralization of MSCs cultured on PEG hydrogel, PEG-Chitosan hydrogel and graphene-chitosan-PEG hydrogel was assessed via Alizarin Red S staining of calcium as shown in FIG. 7. It was observed that extent of mineralization in the MSCs cultured on graphene-chitosan-PEG hydrogel was greater than that in MSCs cultured on PEG hydrogel or Chitosan-PEG hydrogel. These results indicated that graphene in the hydrogel could enhance the osteogenic differentiation of BM-MSCs. Spectrophotometric quantification confirmed these observations. Significantly higher absorbance at 480 nm for BM-MSCs on PEG-chitosan-graphene hydrogel was observed as compared to the absorbance for BM-MSCs on PEG hydrogel and PEG-chitosan hydrogel (data not shown). This represents a 6-fold increase in the extent of mineralization in the BM-MSC cultured on PEG-chitosan-graphene hydrogel compared to BM-MSC s PEG hydrogel.

Osteogenic differentiation and mineralization of bone marrow stromal (BMS) cells usually depends on the cells' interactions with bioactive peptides associated with the matrix proteins. The RGD peptides of ECM proteins interact with BMS cells through integrin surface receptors to facilitate cell spreading and adhesion. The BMP peptide corresponding to residues 73-92 of bone morphogenetic protein-2 can promote differentiation and mineralization of BMS cells. In the prior art, RGD peptide or BMP peptide had to be incorporated into a hydrogel to facilitate osteogenic differentiation of BM-MSCs (He, X. Z. & Ma, J. Y., Langmuir (2008) 24, 12508; Roostaeian, J. et al., J. of Surgical Research (2006) 133, 76]). However, the PCG hydrogel described herein did not require the addition of either of these peptides in order to facilitate osteogenic differentiation of BM-MSCs.

The minerals formed within the PCG hydrogel matrix were further visualized using SEM (data not shown). The morphology of minerals deposited within the hydrogel was imaged with scanning electron microscopy (SEM). Calcium phosphate particles were extensively deposited on the surface of cells and the PCG hydrogel matrix.

When transplanted in vivo, human MSCs cells can be exposed to low oxygen concentration because physiological oxygen tension in a bone fracture is very low (i.e. about 1% $O_2$) due to the disruption of the host vascular system (Potier, E. et al., Bone (2007) 40, 1078; Brighton, C. T. & Krebs, A. G. J. of Bone and Joint Surgery-American Volume A (1972) 4, 323; Heppenstall, R. B. et al., Clinical Orthopaedics and Related Research (1975) 357). Therefore, the osteogenic differentiation of implanted MSCs in various hydrogels under hypoxic conditions was examined. FIG. 7 demonstrates the osteogenic differentiation of BM-MSC under hypoxic conditions. PCG hydrogel was the most densely stained as compared to PEG hydrogel and PC hydrogel. Compared with normaxia, hypoxia seems to have no significant effect on the mineralization of MSC.

The results provided herein are different from data previously reported. Previously, it was found that osteogenic differentiation of mouse BM-MSC or hMSC was inhibited at 3% oxygen (Potier, E. et al., Bone (2007) 40, 1078; Panyukhin, N. V. et al., Biologicheskie Membrany (2008) 25, 352; Fehrer, C. et al., Aging Cell (2007) 6, 745). Potier et al. reported that temporary exposure of MSCs to hypoxia leads to some osteogenic genes being downregulated and implied that exposure of MSCs transplanted in vivo to hypoxia may affect their bone forming potential [Potier, E. et al., Bone (2007) 40, 1078). However, the data provided herein indicates that a PCG hydrogel could preserve the full osteogenic potential of BM-MSCs for in vivo applications.

Example 5

Chondrogenic Differentiation of Cells Placed on a PCG Hydrogel

Cartilage tissue is a flexible connective tissue composed of chondrocytes in an abundant extracellular matrix (ECM) that is mainly composed of collagen type II, proteoglycan, and aggrecan. Due to the intrinsic biology of cartilage tissues, such as limited blood supply and lack of self-regeneration capacity, current treatment of cartilage lesions are not sufficient to restore normal function (Bhardwaj, N. & Kundu, S. C. Biomaterials (2012) 33, 2848). Stem cell-based tissue engineering represents a promising approach for the repair of cartilage. However, the prior art provides no ideal scaffold for this approach.

Accordingly, the effect of PCG hydrogel on the chondrogenic differentiation of BM-MSC and hMSCs was determined. The process of chondrogenic differentiation of MSCs involves condensation of progenitors, chondrocyte differentiation, and deposition of cartilaginous extracellular matrix (ECM), resulting in the formation of cartilage during chondrogenesis. The chondrogenic differentiation was estimated by Alcian blue staining of the glycosaminoglycans (GAG) present in aggrecan, which forms the major component of extra cellular matrix of the cartilage.

Figure 8:
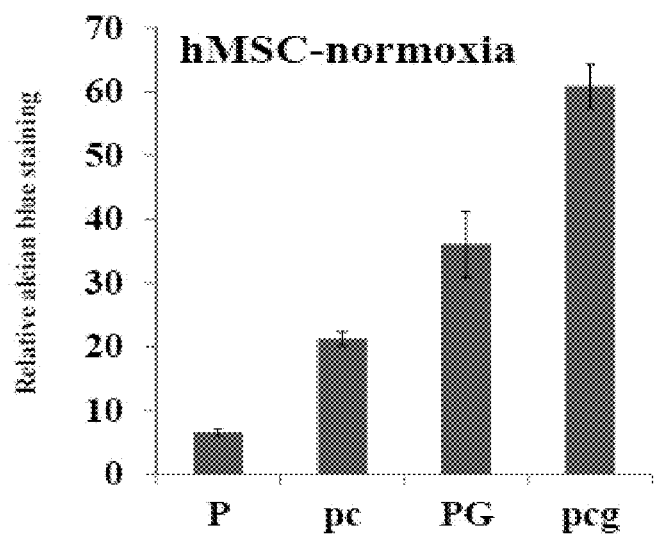
FIG. 8 is a graph showing chondrogenesis of human MSCs (hMSCs) with induction under normoxia. 40k hMSCs were cultured overnight in growth medium on different hydrogels in a 96-well plate under normoxia conditions. On the second day, the growth medium was replenished with differentiation medium. On the seventh day, the cells were stained with alcian blue stain, and area of alcian blue was quantified with imageJ. The differentiation was well defined and sGAG were upregulated on PCG hydrogel when compared to the other hydrogels. M=monolayer, P=PEG hydrogel, PC=PC hydrogel, and PCG=PCG hydrogel.
Figure 9:
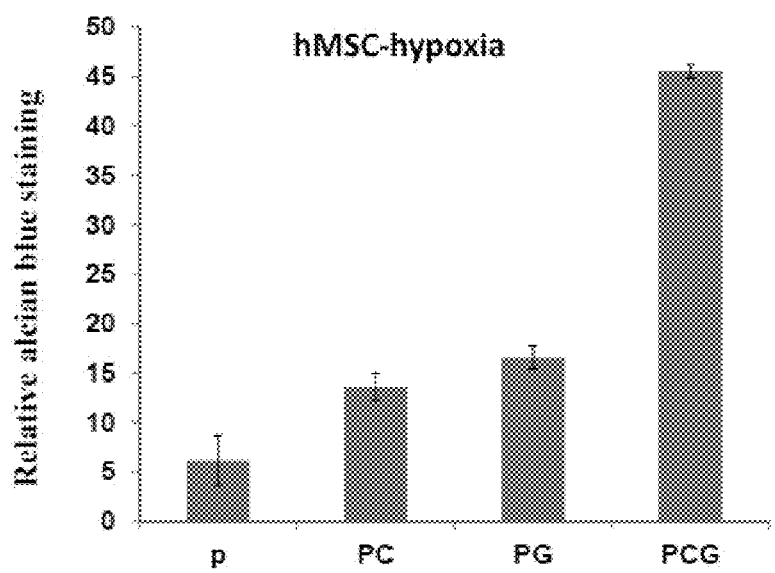
FIG. 9 is a graph showing chondrogenesis of hMSCs with induction under hypoxia. 40k hMSCs were cultured overnight in growth medium on different hydrogels in a 96-well plate under hypoxia conditions. On the second day, the growth medium was replenished with differentiation medium. On the seventh day, the cells were stained with alcian blue stain, and area of alcian blue was quantified with imageJ. The differentiation was well defined and sGAG were upregulated on PCG hydrogel when compared to the other hydrogels. M=monolayer, P=PEG hydrogel, PC=PC hydrogel, and PCG=PCG hydrogel.

The BM-MSCs and hMSCs that were grown on PCG hydrogel were observed to have the most intense blue staining as compared to PEG hydrogel, PC hydrogel and PG hydrogel. These results indicate that chitosan-graphene induces more deposition of glycosaminoglycan and promotes chondrogenic differentiation. FIG. 8 provides a graph demonstrating the results obtained with hMSCs. As shown in FIG. 9, the proteoglycan deposition on PCG hydrogel under hypoxia conditions was significantly greater than that observed under normoxic conditions. The effect of hypoxia on the chondrogenesis of stem cells is dependent on the stem cells type. Hypoxia promotes chondrogenesis in rat mesenchymal stem cells, human embryonic stem cells, and stem cells from the infrapatellar fat pad of osteoarthritis patients (Koay, E. J. & Athanasiou, K. A. Osteoarthritis and Cartilage (2008) 16, 1450; Kanichai, M. et al., J. of Cellular Physiology (2008) 216, 708;) but inhibits chondroprogenitor lineage differentiation of adipose-derived mesenchymal cells (Malladi, P. et al., American J. of Physiology-Cell Physiology (2006) 290, C1139).

Example 6

Preparation and Characterization of TPCG Hydrogel

Figure 10:
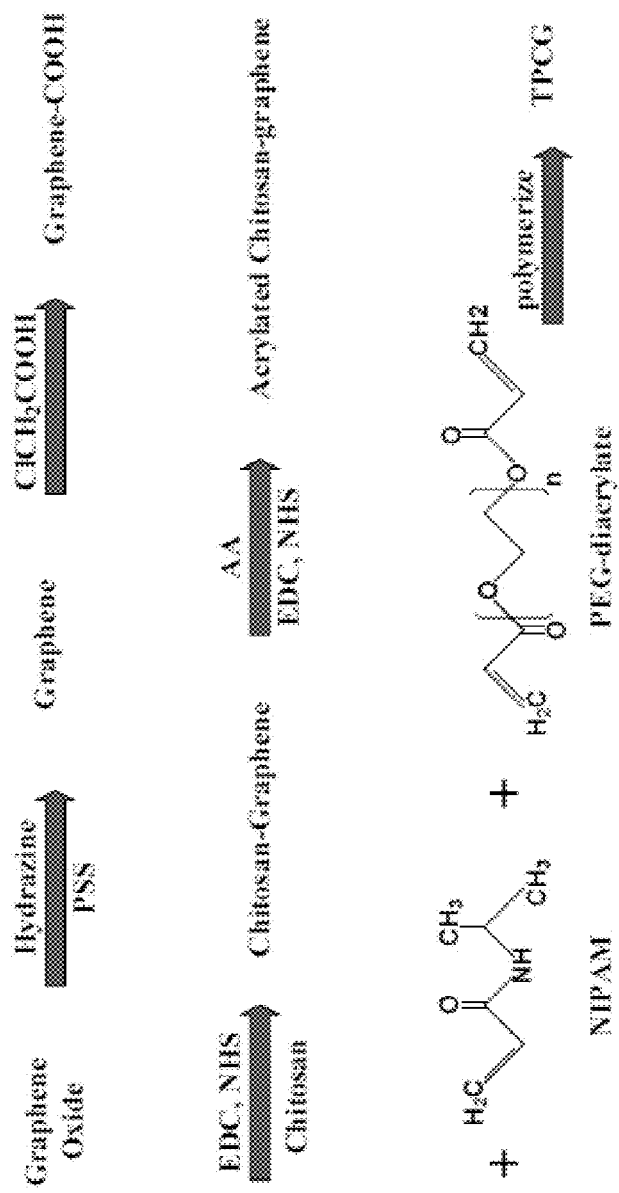
FIG. 10 is a schematic of TPCG hydrogel synthesis.

A TPCG hydrogel was prepared based on a chitosan modified graphene and poly(ethylene glycol) (PEG) according to FIG. 10. To increase the carboxylic acid groups on the surface of graphene sheets, graphene oxide was first reduced to graphene and then reacted with $ClCH_2COOH$. Chitosan was covalently bonded to graphene via amide bonds by reacting the amine groups of chitosan with the COOH groups of graphene in the presence of EDC and NHS. To prevent coagulation, the chitosan functionalized graphene sheet was further reacted with acrylic acid to obtain the acrylated chitosan-graphene monomer. The acrylated chitosan-graphene monomers were copolymerized with NIPAM and PEGDA to form a hydroogel instead of being physically dispersed inside the gel. More specifically, the following materials and methods were used.

Materials

Graphene oxide 0.5% water solution was purchased from Angstron Materials Inc., OH, USA. Water soluble chitosan (Mw 10 kDa) was donated by Transgenex Nanobiotech Inc. Poly(sodium 4-styrenesulfonate) (PSS, Mw 70,000), N-Isopropylacrylamide (NIPAM), acrylic acid anhydrous, polyethylene glycol-diacrylate (PEGDA), ethyl (dimethylaminopropyl) carbodiimide (EDC), N-Hydroxysuccinimide (NHS) were bought from Sigma-Aldrich (St Louis, Mo., USA).

Preparation of Graphene-COOH with Acrylated Chitosan

To prepare graphene-COOH, graphene-COOH was prepared according to the reported procedure with minor modification. PSS-coated reduced GO sheets were prepared by reducing about 50 mL GO (about 1 mg mL$^{-1}$) in the presence of PSS (about 15 mg mL$^{-1}$) and about 1.5 mL hydrazine under refluxing at 100° C. (Stankovich, S. et al., Nature (2006) 442, 282). After cooling to room temperature, about 1.2 g NaOH and about 1.0 g chloroacetic acid were added to the GO-PSS solution and sonicated with 2510 Branson sonicator for about 3 hours (Sun, X. et al., Nano Research (2008) 1, 203) to convert the OH groups to COOH via conjugation of acetic acid moieties, giving graphene-COOH.

To conjugate chitosan to the graphene-COOH, 1 mg/ml graphene-COOH suspensions (about 1 ml, about 2 ml, about 4 ml, about 6 ml) were activated with EDC (about 30 mg) and NHS (about 30 mg) in about 1 ml water for about 30 minutes and added to about 10 ml of water-soluble chitosan solution (about 10 mg/ml) in water. The reaction was kept for about 3 hours at room temperature before dialyzing in a about 12 kDa molecular weight cutoff dialysis bag for about 2 days at room temperature against water.

Finally, acrylated chitosan-graphene was prepared by adding about 1 mL EDC and NHS activated acrylic acid to about 10 mL of the above chitosan-graphene solution. After reacting for about 3 hours, the solution was purified by dialysis in a about 1 kDa molecular weight cutoff dialysis bag for about 2 days at room temperature against water.

Preparation of the TPCG Hydrogel

The TPCG hydrogel was then prepared by adding about 300 mg of NIPAM to about 50 µl of PEGDA and about 1 mL of acrylated chitosan-graphene (about 10 mg/mL) to about 25 ml of nano-pure water in a three-necked flask. The solution was purged with argon gas for about 30-about 45 seconds, and about 25 ml of APS (about 53 mg in about 25 mL) was added drop wise. The solution changed from colorless to white in about 30 minutes and the reaction was continued for about 4 hours. The sample solution was purified by dialysis in a dialysis bag with an about 1 kDa molecular weight cutoff for about 2 days at room temperature against water. Some solution was kept at room temperature for a further thermal sensitivity test. The rest of the purified solution was freeze-dried and kept at about 4° C.

Characterization of the TPCG Hydrogel

The particle morphology of the TPCG hydrogel was spherical and the particle size distribution was monodisperse (data not shown). UV-vis spectroscopy was used to analyze the optical absorption of TPCG compared to graphene. Similar to PEG-functionalized nanographene sheets (Yang, K. et al., Nano Letters (2010) 10, 3318), TPCG exhibited strong optical absorption (data not shown). Compared to the graphene, the apparent increase of absorption in the visible region (400-700 nm) was due to light scattering by the PNIPAM in the nanogel.

Figure 11A:
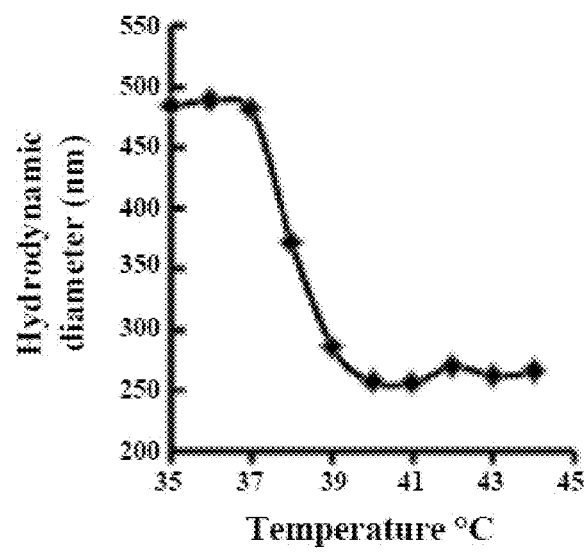
FIGS. 11A-11C contain graphs showing (FIG. 11A) the temperature dependence of hydrodynamic diameter of TPCG.

The temperature-induced change in size of the TPCG was measured by DLS (FIG. 11A) using heat as the stimulus. The TPCG exhibited a thermoresponsive discontinuous phase-transition due to the dehydration of the polymer chains and the collapse of the hydrophilic segments. The diameter of TPCG decreased approximately 220 nm on heating to about 40° C. The size of the dried TPCG (about 35 nm) observed in TEM was much smaller than the size determined by DLS.

The temperature dependence of the phase transition of TPCG was determined turbidimetrically (at 650 nm) by a Lambda 35 UV/vis spectroscopy (Perkin-Elmer, USA) fitted with a 1-cm optical path length quartz cell. The dispersions were diluted and heated from about 35° C. to about 45° C. at a heating rate of about 1° C./minute. The hydrodynamic particle sizes of TPCG were measured from 35° C. to 42° C. using a DynaPro DLS plate reader (Wyatt Technology, Germany). The morphology of the TPCG was determined by transmission electron microscopy (TEM).

Figure 11B:
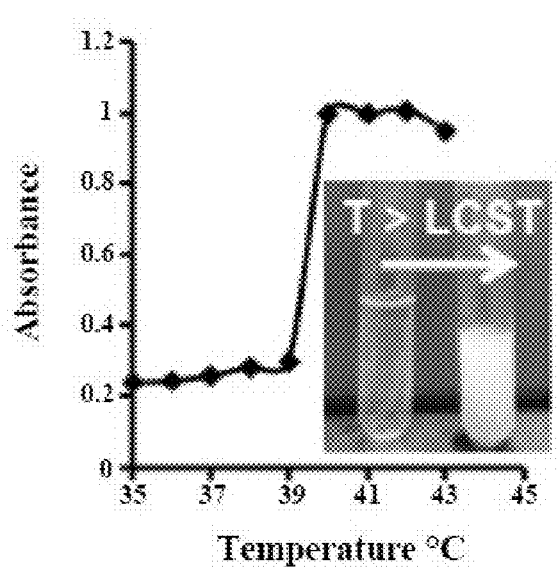
Figure 11C:
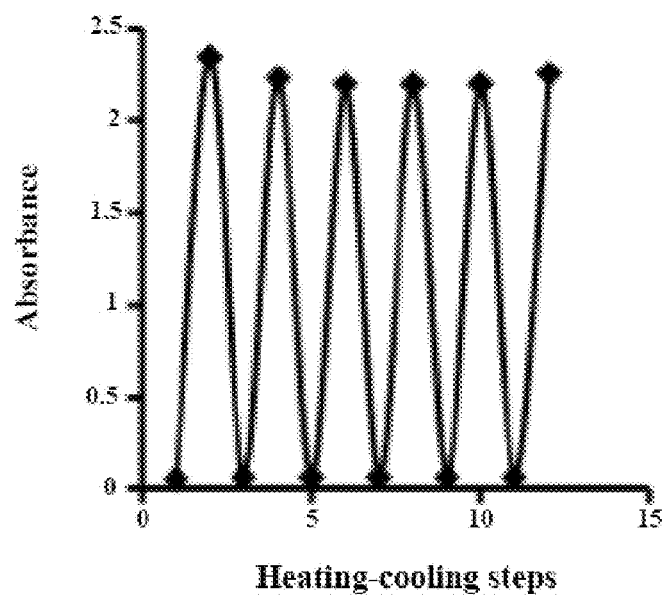

The thermosensitive behavior of TPCG at physiological temperatures was also evaluated by monitoring the turbidity change of aqueous TPCG solutions upon temperature change (FIG. 11B). The turbidity of TPCG solution was observed to increase rapidly with increasing temperature from about 39° C. to about 42° C. When the temperature reached about 42° C., the hydrogel began to shrink and water molecules were squeezed out of the hydrogel. The difference in the refractive index between the hydrogel and water increased, thus causing the increased turbidity. During cooling/heating cycles, the turbidity of the sample at about 40° C. or about 25° C. remained the same (FIG. 11C), suggesting that the turbidity changes with temperature were reversible.

Example 7

Cytotoxicity of TPCG Hydrogel

Figure 12:
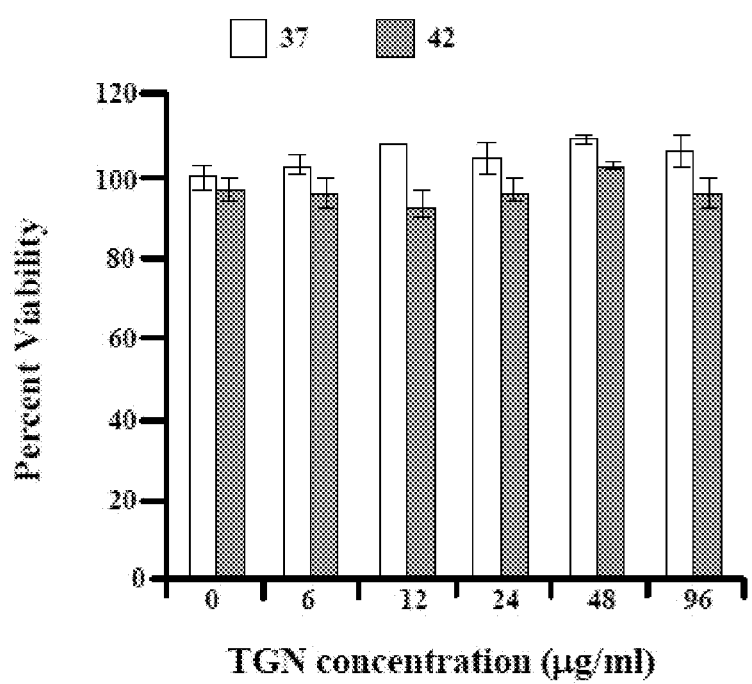
FIG. 12 is graph showing the viability of TRC1 cells treated with different concentrations of TPCG (referred to as TGN) at 37° C. for 72 hours, or 30 minutes at 42° C. then 37° C. for 72 hours.
Figure 13A:
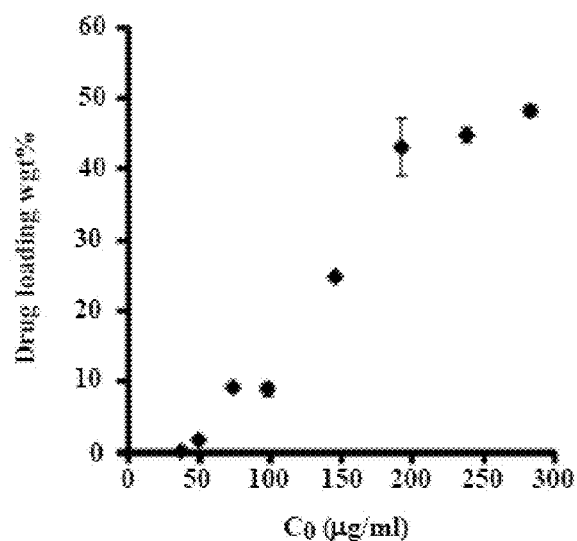
FIGS. 13A-13B contains graphs showing (FIG. 13A) the drug loading as percentage of TPCG.
Figure 13B:
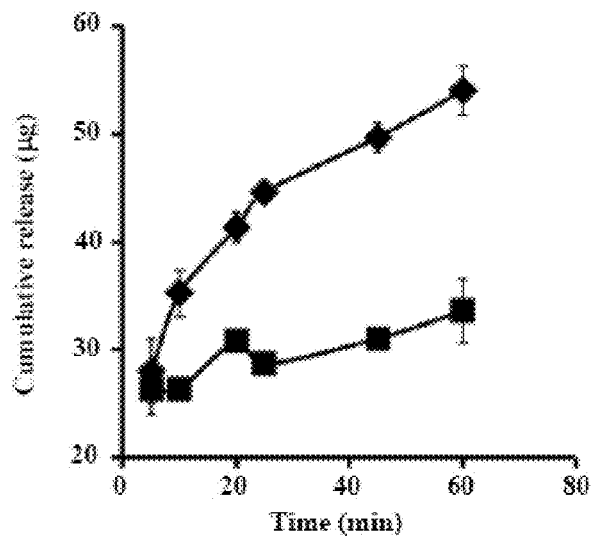

To evaluate the potential application of this reversible thermal responsiveness of TPCG, its biocompatibility was assessed by testing the cytotoxicity of TPCG on a mouse prostate cancer cell line, TRC1. FIG. 12 demonstrates the viability of TRC1 cells exposed to different concentrations of TPCG, expressed as a percent of cell survival without TPCG. There was no observed decrease in cell viability observed upon exposure to high concentration of TPCG. To test for possible effect of hydrogel heating on cell viability, the cells were treated with different concentration of TPCG at about 42° C. for about 30 minutes and then returned to 37° C. The viability of cells incubated at 42° C. remained similar to those cultured at 37° C. (FIG. 12).

More specifically, TRC1 mouse prostate cancer cells were cultured in Dulbecco's modified Eagle's medium containing about 4.5 g/L D-glucose, about 110 mg/L sodium pyruvate, and about 200 mM L-glutamine supplemented with about 5% fetal bovine serum and about 1% penicillin and streptomycin. In vitro cytotoxicity of TPCG was evaluated using the PrestoBlue® cell viability reagent (Life technology Frederick, Md.). Cells were seeded on 96-well plates (about 15,000 cells per well) and grown at about 37° C. in a humidified atmosphere containing about 5% $CO_2$ for about 1 day to allow adherence. Various concentrations of TPCG were added to the wells in triplicate. The cells were cultured for about 72 hours at about 37° C. under about 5% $CO_2$. After about 72 hours, about 10 µL of PrestoBlue® reagent was added to each well and cells were incubated for about 10 minutes. Cell viability was determined by measuring absorbance at 535 nm in a microplate reader (Synergy H4, Biotek). Cell viability (%) was calculated according to the following equation: Cell Viability (%)=(A535 sample)/(A535 control)×100.

Example 8

Drug Loading and Release of TPCG Hydrogel

Figure 14A:
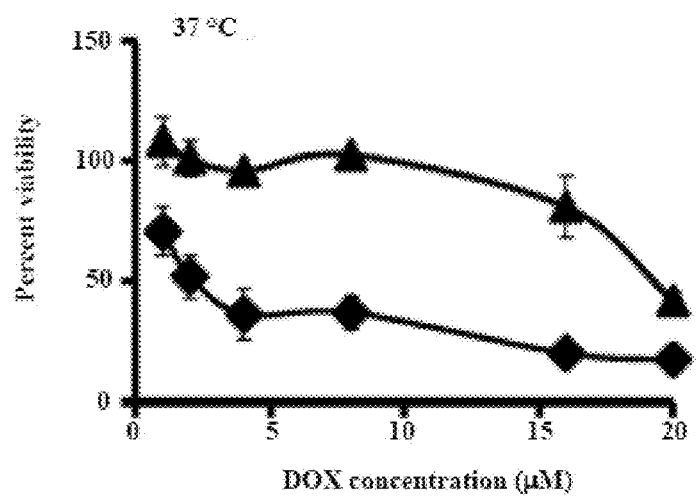
FIGS. 14A-14B contain graphs showing the viability of TRC1 cells treated with different concentrations of DOX (♦) or DOX-TPCG (▲) at 37° C. for 72 hours (FIG. 14A), or 42° C. for 30 minutes then 37° C. for 72 hours (FIG. 14B).
Figure 14B:
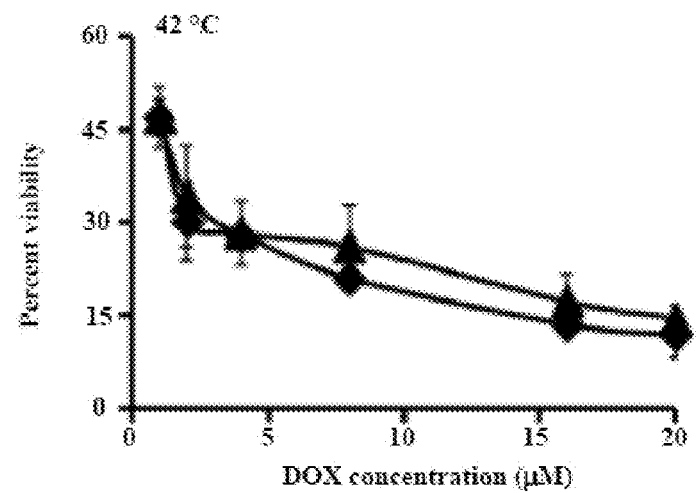

For drug loading and release studies of the TPCG hydrogel, freeze-dried TPCG nanoparticles (about 1 mg) were mixed with different concentrations of DOX solution at 4° C. overnight. The solution was placed in a dialysis bag (about 1 kDa MWCO) against water to remove free DOX at room temperature for about 2 hours. The dialysis bag with DOX loaded TPCG was placed into about 30 mL phosphate-buffered saline (pH about 7.4) in a 50 mL centrifuge tube. The tube was placed into a water bath at about 37° C. or about 45° C. At various times, about 2 mL was withdrawn from the tubes to measure DOX absorption at 485 nm. The concentration of DOX was calculated from a standard curve of known DOX concentrations. The drug loading content (wt. %) at different DOX starting concentrations is shown in FIG. 14A. The drug loading content increased with DOX feeding concentration because more drug molecules were available for entrapment. The equilibrium drug loading content was found to be 48 wt % of dry TPCG. To determine how temperature influences the release of DOX, DOX-TPCG was incubated at 37° C. and 42° C. FIG. 14B shows the time-dependent release profile of DOX at 37° C. and 42° C.

Example 9

Cellular Uptake and Subcellular Localization of DOX-TPCG

To investigate the DOX release behavior of DOX-TPCG in cells at about 37° C. and about 42° C., TRC1 cells were treated with DOX-TPCG or free DOX (about 4 μM). For cellular uptake and subcellular localization tests, TRC1 cells were seeded (about 60,000 cells per chamber) in four-well chamber CellView™ culture dish (Griener, Bio-one) and grown at about 37° C. overnight. The plates were put in a 3i live cell pathology device at about 37° C. or about 42° C. After the samples (about 4 μM) were added to the cells, the fluorescent images were taken at 0 minutes, about 30 minutes and about 60 minutes with a 3i Olympus Spinning Disk Confocal Microscope (laser, 488 nm).

At about 37° C., both DOX-TPCG and free DOX were internalized into cells after about 30 minutes. After about 60 minutes, an increase in nuclear fluorescence intensity was observed for the free DOX. However, the DOX-TPCG fluorescence was observed exclusively in the cytoplasm. In contrast, when the cells were incubated at about 42° C. for about 30 minutes, an increase in nuclear fluorescence intensity was observed for both free DOX and DOX-TPCG. At about 37° C., DOX remained sequestered inside the hydrogel after internalization of DOX-TPCG, but DOX was released from the hydrogel at 42° C. and entered the nucleus. Compared to 37° C., the cells demonstrated more internalization of both DOX-hydrogel and free DOX at 42° C. (data not shown).

The confocal fluorescence images of TRC1 cells demonstrated that the DOX-TPCG was taken up by cells via the endocytic pathway and transported into the endosome. At 37° C., free DOX was observed in the nucleus after 60 minutes due to the binding of DOX to the nuclear DNA. The fluorescence of DOX-TPCG was only seen in the cytoplasm after 60 minutes, which indicates that DOX is still trapped inside the TPCG particles because of the swollen state at 37° C. At 42° C., the fluorescence intensity in cells was increased for both free DOX and DOX-TPCG after 30 minutes. The reason for the higher DOX levels in cells at 42° C. is unknown, but presumably it is due to increased cellular endocytosis, which has been shown to be both energy- and temperature-dependent. In addition, the fluorescence intensity in the nucleus was increased for both free DOX and DOX-TPCG. These results suggest that DOX was released from the TPCG in the endosome and transported to the nucleus owing to the shrinkage of the hydrogel upon heating.

Example 10

Cytotoxicity of DOX-TPCG Against Cancer Cells in Culture

To determine the cytotoxicity of DOX-TPCG nanogels at 37° C. and 42° C., TRC1 cells were incubated with different concentrations of DOX-TPCG or free DOX at about 37° C. for about 72 hours (FIG. 14A) or by incubating cells with different concentration of DOX-TPCG and free DOX at about 42° C. for about 30 minutes and then incubating them at about 37° C. for about 72 hours (FIG. 14B). More specifically, about 15,000 cells per well were allowed to adhere to a 96-well plate overnight before adding DOX or DOX-TPCG. For testing the thermo-release of DOX from DOX-TPCG, the cells were incubated with DOX-TPCG or free DOX at about 37° C. or about 42° C. for about 30 minutes after which the plates were returned to about 37° C. for about 3 days. Cell viability was determined by Presto-Blue® assay as described above. Viability values were calculated as the fraction of treated cells/untreated cells.

At 37° C., the cytotoxicity of DOX-TPCG was observed to be significantly less than free DOX. The IC50 value of free DOX and DOX-TPCG were about 2 μM and about 20 μM, respectively. At 42° C., DOX-TPCG showed comparable cytotoxicity to free DOX. The IC50 of free DOX and DOX-TPCG was less than about 1 μM.

The cytotoxicity of DOX-TPCG was observed to be much less than free DOX at 37° C. but comparable to free DOX at 42° C. The empty TPCG was not toxic to cells, and heating of cells to 42° C. for 30 minutes did not reduce cell viability. Therefore, the increased cytotoxicity of DOX-TPCG was owing to the faster DOX release from the endosome. This enhancement of cytotoxicity of DOX-TPCG result is in accordance with the result of DOX release behavior from DOX-TPCG inside the cells.

Example 11

Characterization of PCG Hydrogels

To investigate the function of graphene in the hydrogel, PEG (P), PEG-chitosan (PC) and PEG-graphene (PG) hydrogels were prepared as controls. Swelling, degradation, microarchitecture, absorbance capacity and cytotoxicity of four different hydrogels (P, PC, PG, and PCG) were characterized and compared.

Materials

Graphene oxide (about 0.5%) water solution was purchased from Angstron Materials Inc., OH, USA. Water soluble chitosan (Mw, 10 kDa) was donated from Transgenex Nanobiotech Inc. Poly (ethylene glycol) diacrylate (PEG-diacrylate), Tetramethylethylenediamine (TEMED), graphene oxide, Ammonium persulfate (APS), acrylic acid anhydrous, ethyl (dimethylaminopropyl) carbodiimide (EDC), N-Hydroxysuccinimide (NHS), Methods Preparation of the Hydrogels:

The acrylated-chitosan-chemically reduced graphene oxide was prepared according to the methods described elsewhere herein. See e.g. FIG. 10. See also Wang et al. Nanomed., Nanotechnol., Biol., and Med. 2013:9. Acrylated chitosan was prepared by adding EDC and NHS activated acrylic acid (about 10 µl) to about 10 mL chitosan solution (about 150 mg). The purification procedure was the same as the acrylated chitosan-chemically reduced graphene oxide. To prepare the PCG hydrogel, about 450 µl of 1 mg/mL of acrylated chitosan-graphene solution was added to about 956 µl deionized water in a 2 mL centrifuge tube. Next, about 45 µl of about 10 wt % APS and PEG-diacrlyate was added to the tube. The solution was mixed well by vortexing. After purging the solution with argon gas for about 30 s, about 4 µl of TEMED was added to the solution and vortexed for about one second. For a 96-well plate, about 75 µl of the solution was added to each well. The solution was left for about 5 min to form the PCG hydrogel in each well. The P hydrogel, PC hydrogel and PG hydrogel were prepared similarly except instead of adding acrylated chitosan-graphene solution, about 450 µl of water, about 1 mg/ml acrylated chitosan, or graphene solution, respectively was added. After forming the hydrogel in each well, about 200 µl of deionized water was added to each well to wash the hydrogel for about three days. Before the cells were plated onto the hydrogels, the hydrogels were sterilized for by exposing the hydrogels to UV light for about 2 hours. After sterilization, the hydrogels were washed one time with DMEM.

Sorption Experimental Protocols.

Hydrogel samples were freeze-dried for one day and stored in a desiccator at room temperature. The sorption behavior of the hydrogels was monitored by detecting the increase in mass of the samples at different time intervals on an electronic balance. In a typical sorption experiment, a pre-weighed dry gel pellet was immersed into water at 24±1° C. water bath. At prescribed time intervals, the hydrogel was taken out of solution and weighed after wiping off the excess water from the surface with Kimwipe paper (Kimberly Clark Professional). The sorption degree, SD, of hydrogels was defined as follows: SD %=$(W_t-W_d) \times 100/W_d$=$M_t \times 100/W_d$ where $W_d$ is the weight of the dry gel, $W_t$ is the weight of wet hydrogel at each time interval, and Mt is the gain in the weight of the dry gel at time t.

The hydrogel samples obtained by the above method were cut and freeze-dried to determine the morphology via scanning electron microscopy (JEOL, JSM-6490LV).

In Vitro Degradation of PCG Hydrogel Protocols:

To determine the degradation behavior of PCG hydrogels for their application to rgenerative medicine in vivo, in vivo degradation under accelerated conditions was examined. Briefly, PCG hydrogels were incubated with lysozyme and the degradation kinetics were compared to those in the presence of vehicle (PBS) only. The degree of degradation was estimated in terms of change of dry weight of the hydrogel. More specifically, gels were incubated in 1×PBS (pH7.4) or about 1 mg/ml lysozyme PBS solution at about 37° C. for about 21 days. The prepared hydrogel was washed with deionized water and then lyophilized. The weights of the dry gel were weighed ($W_{d0}$). Then the gels were placed into phosphate buffered saline (PBS) or 1 mg/ml lysozyme/PBS solution at 37° C. The hydrogels were taken out at different time points and were freeze-dried and weighed again ($W_{dt}$). The weight loss % was calculated as follows:

Weight loss %=$(W_{d0}-W_{dt}) \times 100\%/W_{d0}$

Cell Viability and Morphology Assay and Protocols:

The morphology and viability of MSCs on the hydrogel matrix were determined using the Live-Dead assay kit (Invitrogen) 3 or 5 days after seeding MSCs at a density of about 20,000 cells/well onto the hydrogel. The cell-hydrogel samples were rinsed with sterile PBS and stained with calcein Am and ethidium bromide. Samples were immediately examined with an Olympus ix71 inverted fluorescence microscope. Calcein AM permeates the plasma membrane of viable cells and produces green fluorescence. Ethidium bromide enters cells with damaged membranes, binds to fragmented nucleic acids, and produces red fluorescence in dead cells.

PrestoBlue® cell viability reagent (Invitrogen) was used to examine the cell viability 3 days after seeding BM-MSCs at a density of about 10,000 cells/well on 96-well plates or on hydrogels in 96-well plates. Experiments were carried out in triplicate.

Statistics:

All quantitative data are presented as mean±STDEV. Statistical analyses were performed using Student's t test. A statistical difference is defined as $p<0.05$.

Results

Figure 15A:
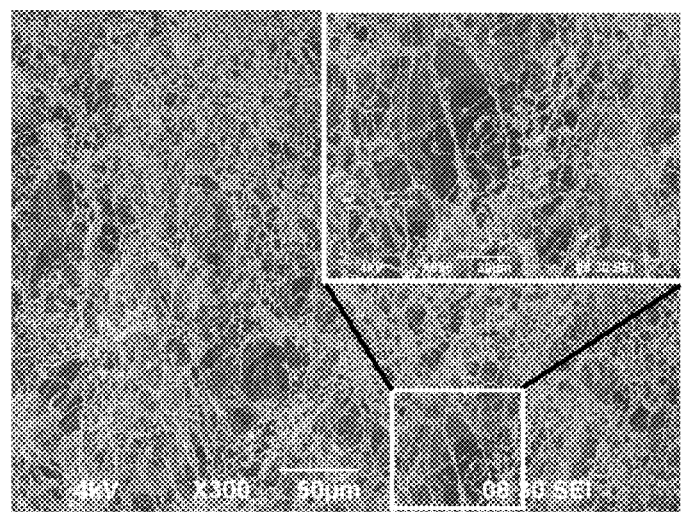
FIGS. 15A-15G demonstrate SEM photographs of a freeze-dried PCG hydrogel (FIG. 15A), and freeze-dried control hydrogels: PEG (P) (FIGS. 15B-15C), PEG-Chitosan (PC) (FIGS. 15D-15E), and PEG-Graphene (PG) (FIGS. 15F-15G).
Figures 15B, 15C, 15D, 15E, 15F, 15G:
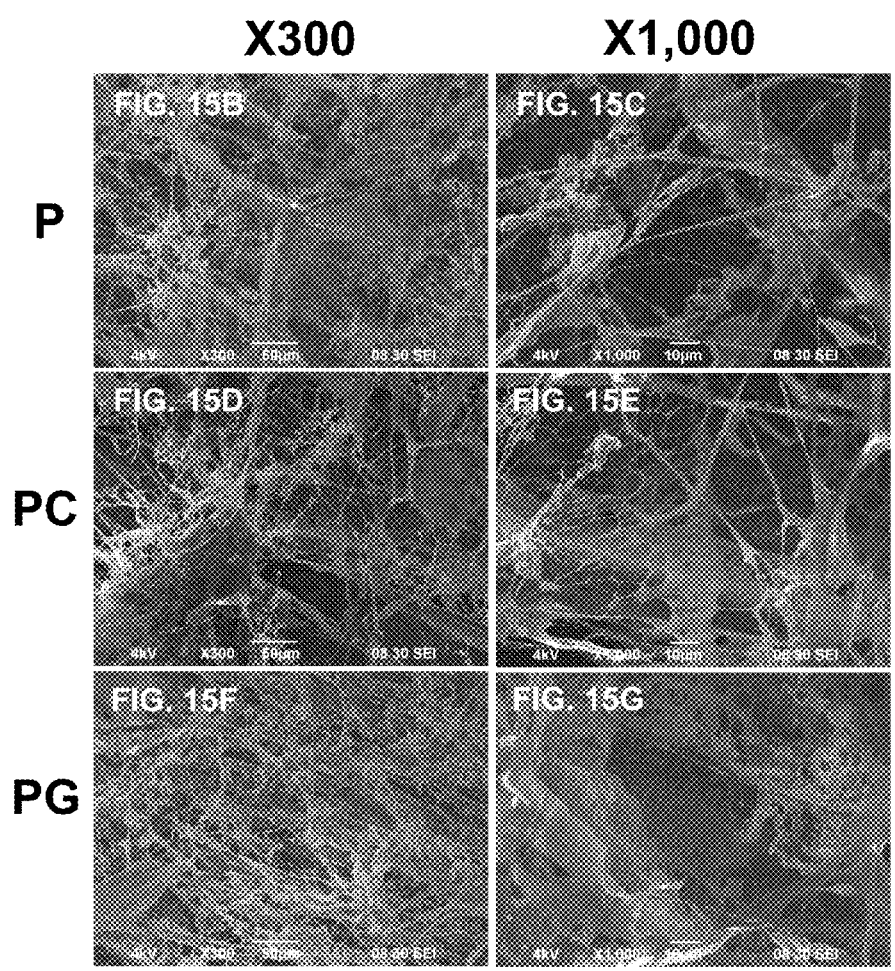
Figures 17A, 17B, 17C, 17D:
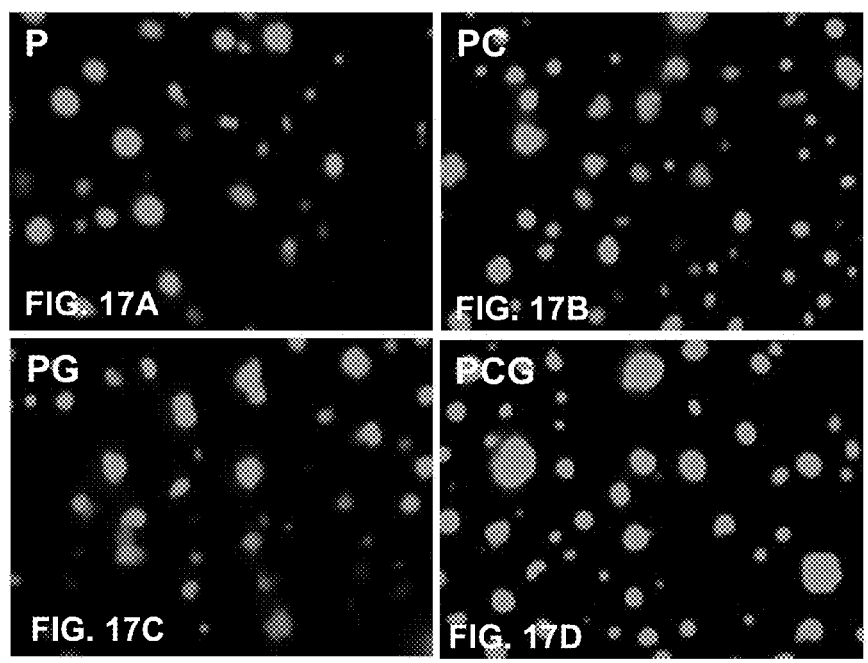
FIGS. 17A-17D demonstrate the cell morphology of BM-MSCs grown on a PCG hydrogel (FIG. 17D) or control hydrogels: P (FIG. 17A), PC (FIG. 17B) and PG (FIG. 17C) hydrogels. Cell morphology was examined after about 3 days in culture on the hydrogels in proliferation medium. Cells were stained with calcein-AM/ethidium homodimer, which stains live cells green and dead cells red. Cells were visualized using fluorescence microscopy at 200× magnification.

Hydrogel Architecture:

To determine the inner morphology by SEM, 10 µm thick sections were cut from hydrogel samples and freeze-dried. FIG. 15A shows the fibrillar network of a cross-section from a PCG hydrogel. The sample was highly heterogeneous with both thick and thin fibers. The control hydrogels (P, PC, PG) were less uniform than PCG hydrogel and displayed inner networks with thick fibers and large pieces (FIG. 15B-15G). The microarchitecture of a PCG hydrogel is very similar to the extracellular matrix (ECM) and thus should permit nutrient transport.

Swelling Rate:

The swelling rate of P, PC, PG and PCG hydrogels is shown in FIG. 2. The swelling rate of each of the four hydrogels was observed to be fast at the beginning of the measurement time and then leveled off. The P and PC hydrogels achieved equilibrium within about 1 hour. However, the PG and PCG took about 6 hours to reach equilibrium. PC hydrogels were observed to have a greater equilibrium swelling degree than that of P hydrogels. The degree of swelling of PCG hydrogels at equilibrium is much greater than the P, PC, or PG hydrogels.

Degree of Degradation:

Differentiation of BM-MSCs can rely on factors, such as dexamethasone and ascorbic acid. Therefore the adsorption capacity of hydrogels for these nutrients was evaluated. FIGS. 16A and 16B demonstrate the dexamethasone and ascorbic acid absorption potential in different hydrogels. Compared to P, PC, and PG hydrogel, PCG hydrogel demonstrated greater dexamethasone and ascorbic acid absorption capacity. FIG. 4 demonstrates the results from the lysozyme-mediated degradation of the PCG hydrogel. In about 14 days, no significant degradation in PBS was observed. In contrast, about a 13.2% weight loss was observed in lysozyme-treated PCG hydrogel. From about day 14 to about 21, PCG hydrogels showed up to 1.5% weight loss in PBS, but very little further degradation in lysozyme.

Cell Adhesion, Viability, and Morphology

Figure 18:
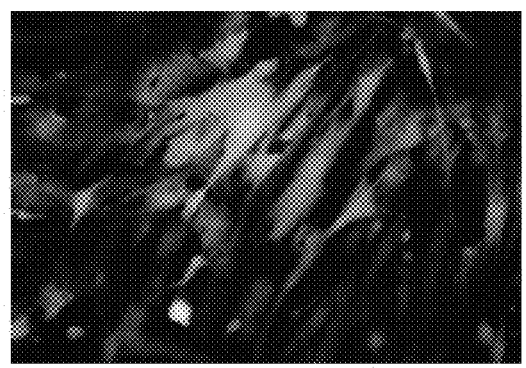
FIG. 18 demonstrates the cell morphology of BM-MCs grown on a monolayer.
Figure 19:
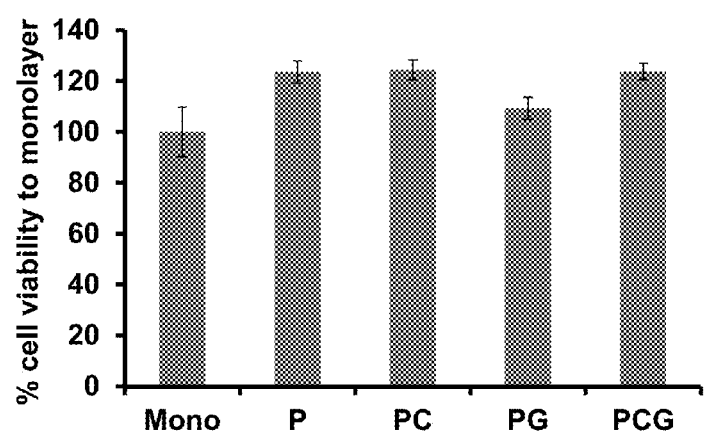
FIG. 19 shows a graph which demonstrates the cell viability of BM-MSCs cultured on different hydrogels (P, PC, PG, and PCG) or a monolayer.

The cell adhesion to hydrogels was imaged with calcein AM staining after three days culture in proliferation medium as shown in FIGS. 17A-17D. The cells were well attached to the hydrogel and demonstrated a rounded shape compared to the spindle shape on monolayers (FIG. 18). No significant difference in cell viability between hydrogels and monolayers was observed, suggesting that the hydrogel does not affect cell survival (FIG. 19).

The effects of longer culture times on the interaction of cells with different hydrogels are demonstrated in FIGS.

Figures 20A, 20B, 20C, 20D:
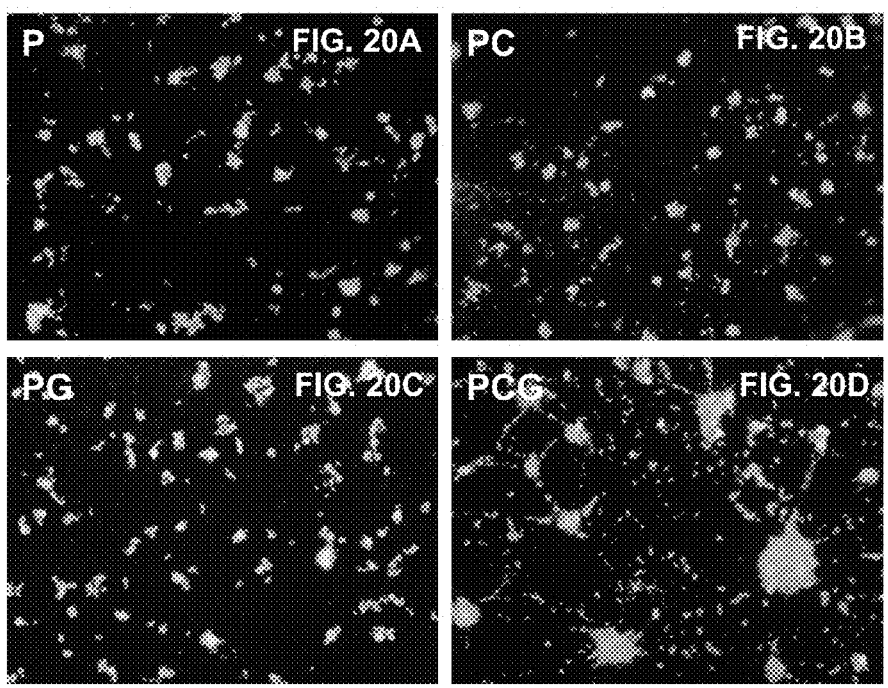
FIGS. 20A-20D demonstrate the cell morphology of BM-MSCs cultured on P, PC, PG, or PCG hydrogels after 5 days of culture in proliferation medium. Cells were stained with calcein-AM/ethidium bromide, which stains live cells green and dead cells red. Cells were visualized using fluorescence microscopy at 100× magnification.
Figures 21A, 21B, 21C, 21D:
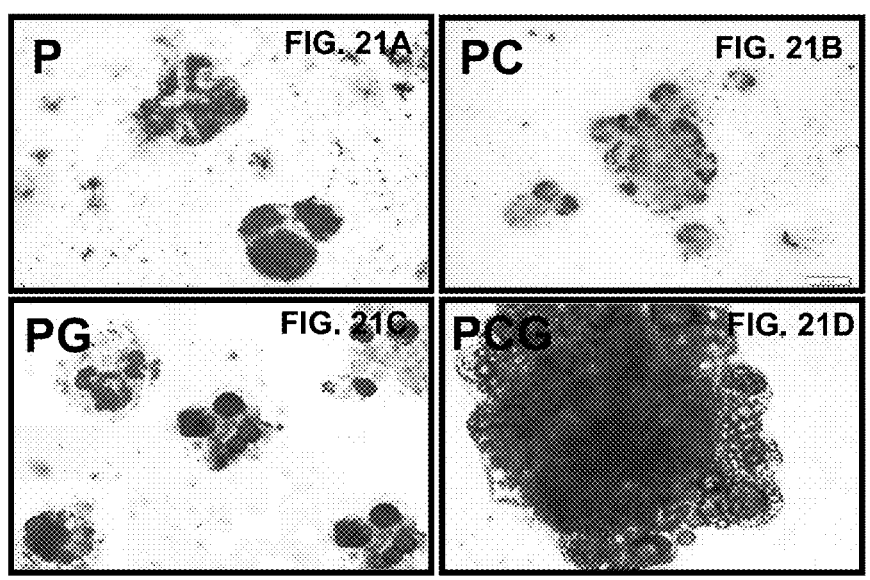
FIGS. 21A-21D demonstrate adipogenic differentiation of mouse BM-MSCs on P (FIG. 21A), PC (FIG. 21B), PG (FIG. 21C), or PCG (FIG. 21D) hydrogels. Mouse BM-MSCs were cultured overnight on the hydrogels in a 96-well plate. From about day 2 in culture, adipocyte differentiating medium was added to the cells. On about day 7 in culture the cells were stained with Oil red O of intracellular lipid droplets and visualized using microscopy at 200× magnification.
Figure 22:
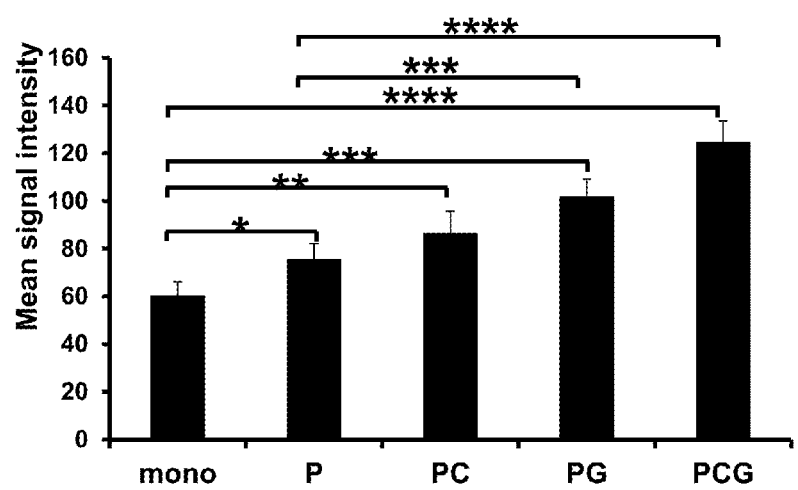
FIG. 22 shows a graph demonstrating the quantification of adipogenic differentiation by Image J that is based on measuring the mean signal intensity of Oil Red O red pixels, (n=5).

20A-20D. After about five days in culture, the BM-MSCs on P (FIG. 20A) or PG (FIG. 20B) hydrogels aggregated to form small clusters. The BM-MSCs tended to aggregate to form small spheroids on PC hydrogels (FIG. 20B), but larger spheroids on PCG hydrogel (FIG. 20D).

Example 12

Differential Potential of BM-MSC on PCG Hydrogels

The adipogenic, osteogenic and chondrogenic differentiation potential of BM-MSCs in the hydrogels of Example 11 were also examined.

Methods

The hydrogels were prepared as in Example 11.

Adipogenic Differentiation:

BM-MSCs (about 40,000) were plated on each hydrogel-containing or control 96-well plate. The cells were cultured at 37° C. in a humidified 5% $CO_2$ atmosphere for overnight. From the second day, STEMPRO™ adipogenesis differentiation medium (Invitrogen) was added to each well and replaced about every two days. After about seven days of induction, the cells were rinsed with PBS, fixed with about 4% formaldehyde for about 30 min, and stained with oil red O (Sigma Aldrich). The stained cells were viewed under the microscope.

Chondrogenic Differentiation:

BM-MSCs (about 40,000) were plated on each hydrogel-containing or control 96-well plate. The cells were cultured overnight at about 37° C. in a humidified atmosphere having about 5% $CO_2$. From about the second day, STEMPRO™ chondrogenesis differentiation medium (Invitrogen) was added to each well and replaced about every two days. After about seven days under differentiation conditions, the cells were rinsed with PBS and fixed with about 4% formaldehyde for about 30 min. After fixation, the cells were stained with about 1% alcian blue prepared in about 0.1 N HCl for about 30 min, washed and visualized under the microscope. After taking pictures, the stain was solubilized with about 6M guanidine hydrochloride for about 8 h at room temperature. Absorbance was measured with a spectrophotometer at 620 nm.

Osteogenic Differentiation:

BM-MSCs (about 40,000) were plated on each hydrogel-containing or control 96-well plate. The cells were cultured overnight at 37° C. in a humidified 5% $CO_2$ atmosphere. From the second day, STEMPRO™ chondrogenesis differentiation medium (Invitrogen) was added to each well and replaced every two days. After seven days induction, cells were rinsed with PBS and fixed in about 4% formaldehyde for 30 min. After fixation, the cells were rinsed twice with PBS and stained with about 2% alizarin red (Sigma-Aldrich) for about 20 min. The unstained alizarin red was washed out with PBS, and cells were visualized under the microscope (IX81, Olympus Inc.).

To confirm the presence of osteogenic differentiated BM-MSCs in the hydrogel, sections from hydrogel-cell matrices were cut, freeze-dried and observed by scanning electron microscopy (SEM) (JEOL, JSM-6490LV). To assay for deposited calcium after osteogenic differentiation of BM-MSCs, energy dispersive X-ray analysis (EDXA-Gensis, JEOL) was performed on the dried hydrogel-cell samples in different locations.

ALP Enzyme Activity:

ALP enzyme activity of BM-MSCs on hydrogels after about seven days osteogenic differentiation was measured on 96-well plates in triplicate. The cells were rinsed twice with Tyrode's balanced salt solution (TBS, about 50 mM Tris base, about 0.15 M NaCl, pH about 7.4), and incubated with about 5 mM p-nitrophenyl phosphate (p-nitrophenyl phosphate disodium salt, Fisher) solution in glycine buffer (about 50 mM glycine, about 1 mM $MgCl_2$, pH about 10.5) for about 60 min at about 37° C. The absorbance of the reaction product, p-nitrophenol, was determined at 405 nm using a UV-Vis spectrophotometer. The standard curve was generated by consecutively diluting about 10 mM p-nitrophenol (Fisher) solution in glycine buffer at concentrations from about 0.1 to about 50 µM. The total protein amount in each well was measured by BCA™ Protein Assay kit (Fisher). The ALP activity was calculated and expressed in units/g protein. (One unit will hydrolyze about 1 mM of p-nitrophenyl phosphate per min at pH about 10.5.)

Immunofluorescent Staining:

The fluorescence immunostaining of PPARγ, collagen II and osteopontin was performed according to the manufacture's protocol. After four days differentiation, hydrogel-cell samples were fixed with 4% paraformaldehyde for 30 min, permeabilized with 0.1% Triton X-100 for 10 min, and blocked with 1% BSA in PBS for one hour. For immunostaining, samples were incubated with primary antibodies (rabbit anti-PPARγ polyclonal primary antibody (Abcam) or mouse anti-collagen II monoclonal primary antibody (Abcam) or mouse anti-osteopontin polyclonal primary antibody (R&D) for overnight, then incubated with secondary antibody (goat anti rabbit Alexa Fluor594 for PPARγ, goat anti-mouse Alexa Fluor 594 (Molecular Probes) for collagen II or OPN) for about 2 hours. Nuclear counterstaining was also performed by incubation the cells with DAPI. The stained hydrogel-cell samples were imaged by fluorescence microscopy.

Statistics:

All quantitative data are presented as mean±STDEV. Statistical analyses were performed using Student's t test. A statistical difference is defined as $p<0.05$.

Results

Figure 23A:
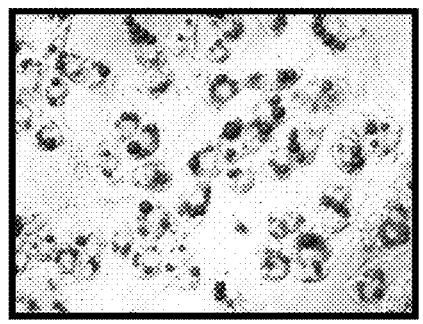
FIGS. 23A-23C demonstrate adipogenic differentiation (FIG. 23A), chondrogenic differentiation (FIG. 23B), and osteogenic differentiation (FIG. 23C) of mouse BM-MSCs cultured on a monolayer. To visualize adipogenic differentiation, cells were stained with Oil Red O. To visualize chondrogenic differentiation, cells were stained with Alcian blue. To visualize osteogenic differentiation, cells were stained with Alizarin Red S.
Figure 23B:
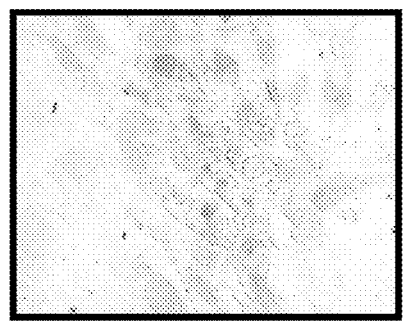
Figure 23C:
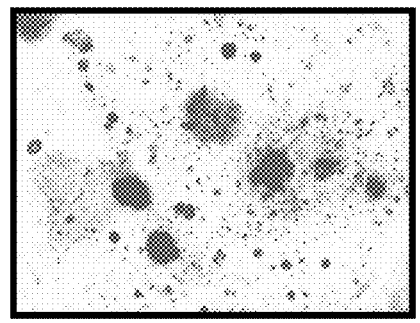
Figures 24A, 24B, 24C, 24D, 24E, 24F, 24G, 24H, 24I, 24J, 24K, 24L:
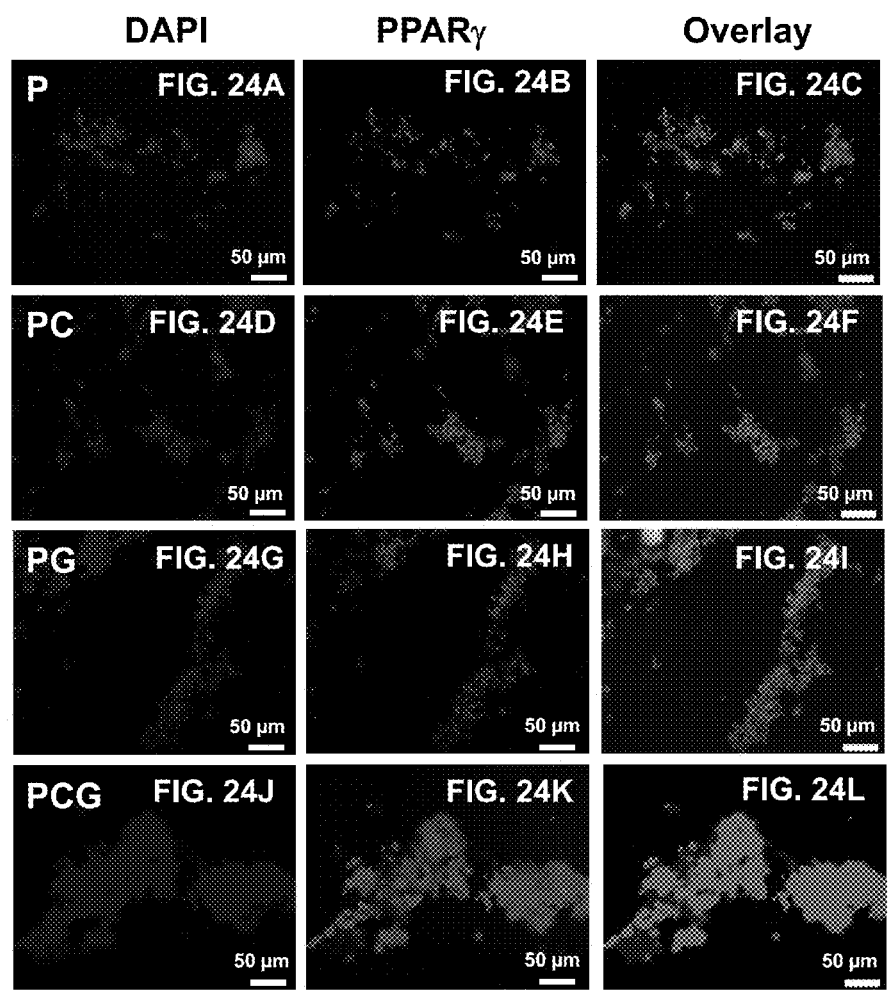
FIGS. 24A-24L demonstrate PPAR-gamma expression in mouse BM-MSCs cultured on P (FIGS. 24A-2C), PC (FIGS. 24D-24F), PG (FIGS. 24G-24I), or PCG (FIGS. 24J-24L) hydrogels in a 96-well plate after three days of induction with adipocyte differentiating medium. After three-days induction, cells were fixed and counter stained with the combination of DAPI (blue) (FIGS. 24A, 24D, 24G, and 24J) and PPAR-gamma (Alexa-Fluor 594, red) (FIGS. 24B, 24E, 24H, 24K). The overlay of the images are shown in FIGS. 24C, 24F, 24I, and 24L.
Figure 25:
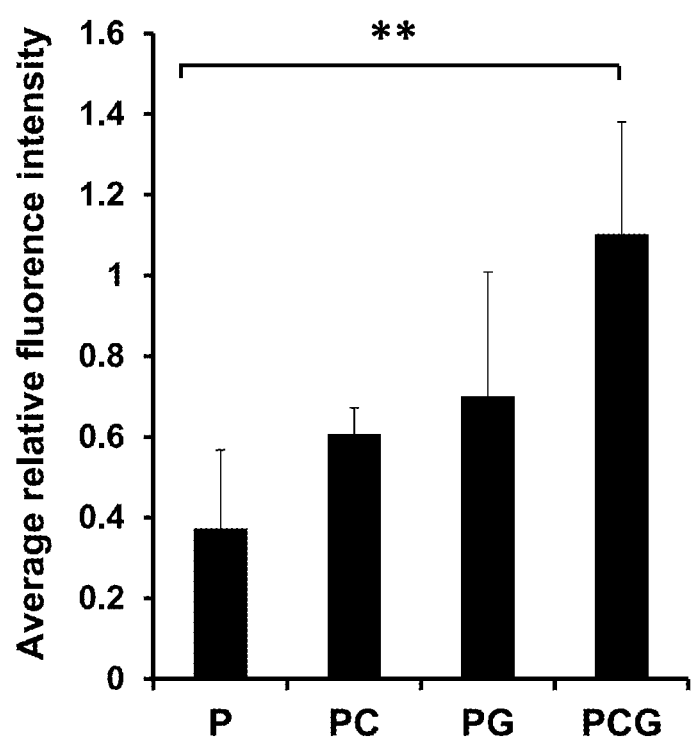
FIG. 25 shows a graph demonstrating quantification of PPAR-gamma by Image J was based on measuring the total integrity density of PPAR-gamma red pixels followed by normalizing to total integrity density of DAPI blue pixels.
Figures 26A, 26B, 26C, 26D, 26E, 26F, 26G, 26H, 26I, 26J, 26K, 26L:
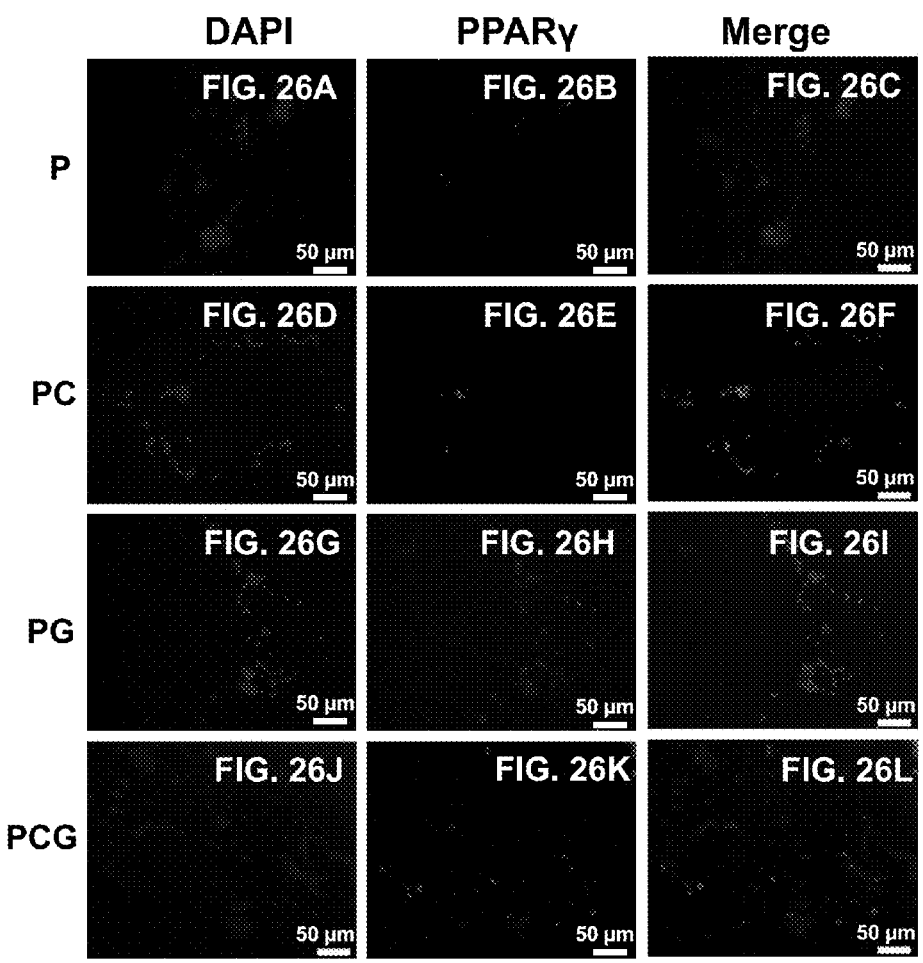
FIGS. 26A-26L demonstrate BM-MSCs cultured on P (FIGS. 26A-26C), PC (FIGS. 26D-26F), PG (FIGS. 26G-26I), or PCG (FIGS. 26J-26L) hydrogels. After four days in culture without induction with differentiation medium, BM-MSCs were fixed, and counter-stained with PPAR-gamma (FIGS. 26B, 26E, 26H, and 26K) (Alexa Fluor 594, red) with the combination of DAPI staining for nuclear localization (FIGS. 26A, 26D, 26G, and 26J). The merged images are shown in FIGS. 26C, 26F, 26I, and 26L).

Adipogenic Differentiation:

BM-MSCs can be induced to differentiate to adipocytes. To test the adipogenic differentiation of BM-MSCs on the different hydrogels, the oil red O staining of intracytoplasmic lipids and immunohistochemistry staining of PPARγ were determined (FIGS. 21A-21D and 22). Compared to monolayers (FIGS. 23A-23C), all 3D hydrogels demonstrated significantly greater oil red staining (FIGS. 21A-21D and 22). PEG hydrogels have been studied as scaffolds to encapsulate human BM-MSC for facilitating adipogenic differentiation both in vitro and in vivo. Here, compared to the control P, PC and PG hydrogels, PCG hydrogels showed the greatest level of oil red O staining.

To determine if the enhancement of the adipogensis by PCG hydrogel is associated with upregulation of PPARγ, we determined the expression of PPARγ by immunofluorescent staining. Immunofluorescence images of BM-MSCs three days after adipogenic induction showed the highest expression level of PPARγ on PCG hydrogels (FIGS. 24A-24L and 25) compared to P, PC, or PG hydrogels. Upregulation of PPARγ was accompanied by correspondingly greater lipid formation. Without the adipogenic induction, however reduced PPARγ expression was observed (FIGS. 26A-26L).

Figure 28:
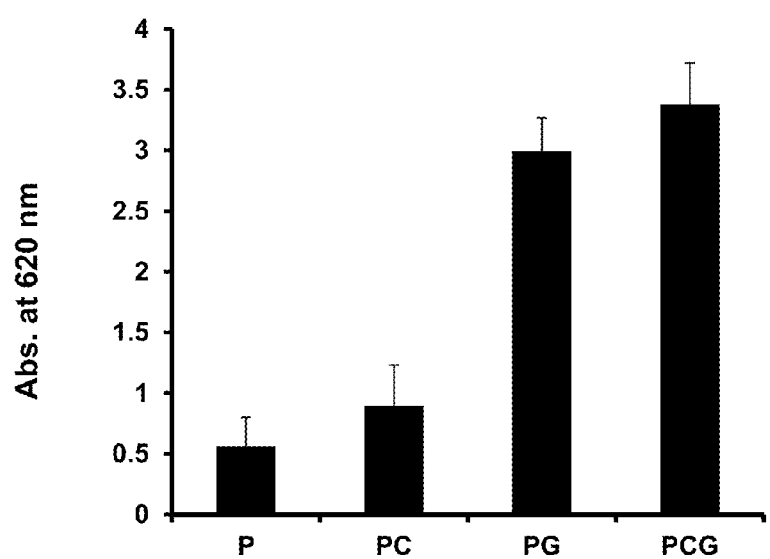
FIG. 28 shows a graph demonstrating the quantification of alcian blue stain extracted from the cultures of FIGS. 27A-27D.
Figures 29A, 29B, 29C, 29D, 29E, 29F, 29G, 29H, 29I, 29J, 29K, 29L:
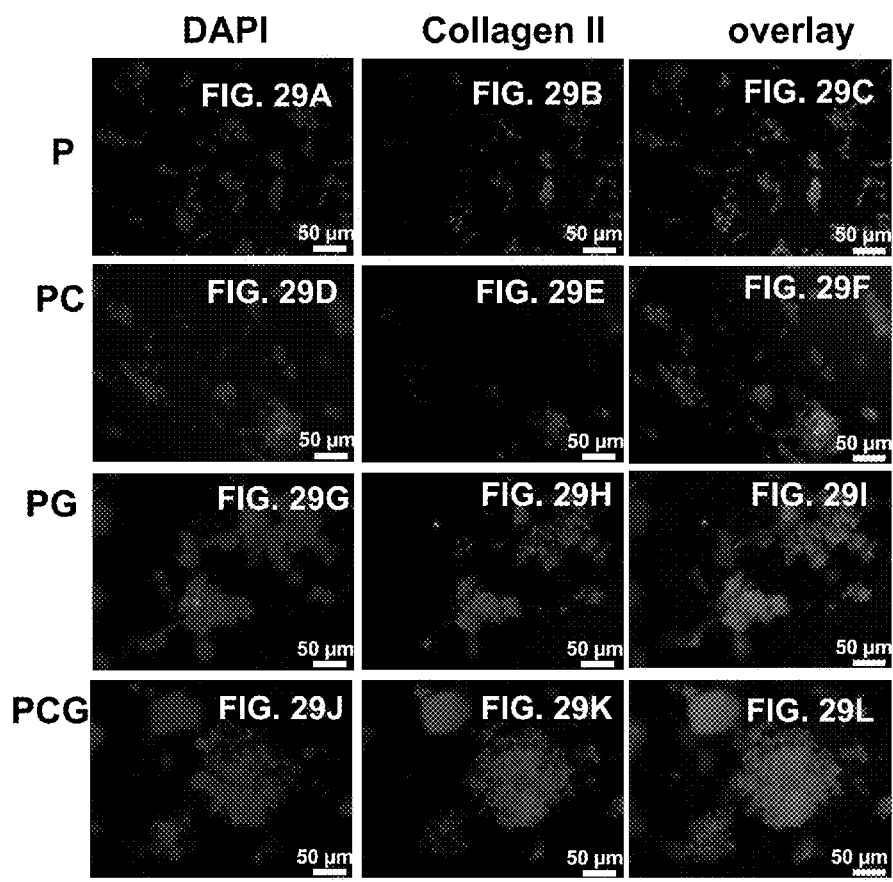
FIGS. 29A-29L demonstrates immunostaining of mouse BM-MSCs cultured on P (FIGS. 29A-29C), PC (FIGS. 29D-29F), PG (FIGS. 29G-29I), or PCG (FIGS. 29J-29L) hydrogels. After 3 days treatment with chondrogenic differentiation medium, cells were stained with DAPI (FIGS. 29A, 29D, 29G, and 29I, blue), or Collagen II (FIGS. 29B, 29E, 29H, and 29Y, red) using a Collagen II antibody. The merged (overlay) images are shown in FIGS. 29C, 29F, 29I, and 29L.
Figure 30:
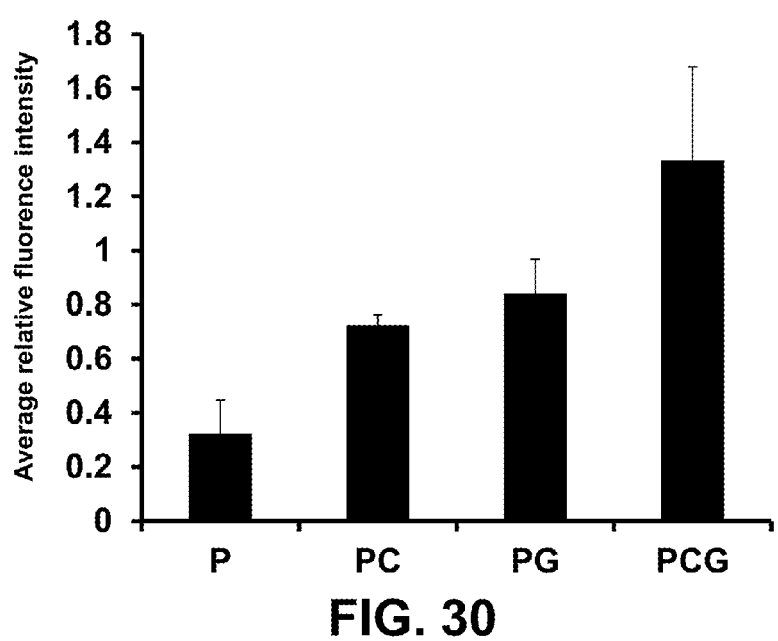
FIG. 30 shows a graph demonstrating quantification of collagen II in the cells of FIGS. 29A-29L. Quantification by Image J was based on measuring the total integrity density of collagen II red pixels and then this numerical value was normalized to the total integrity density of DPI blue pixels in the image.
Figures 31A, 31B, 31C, 31D, 31E, 31F, 31G, 31H, 31I, 31J, 31K, 31L:
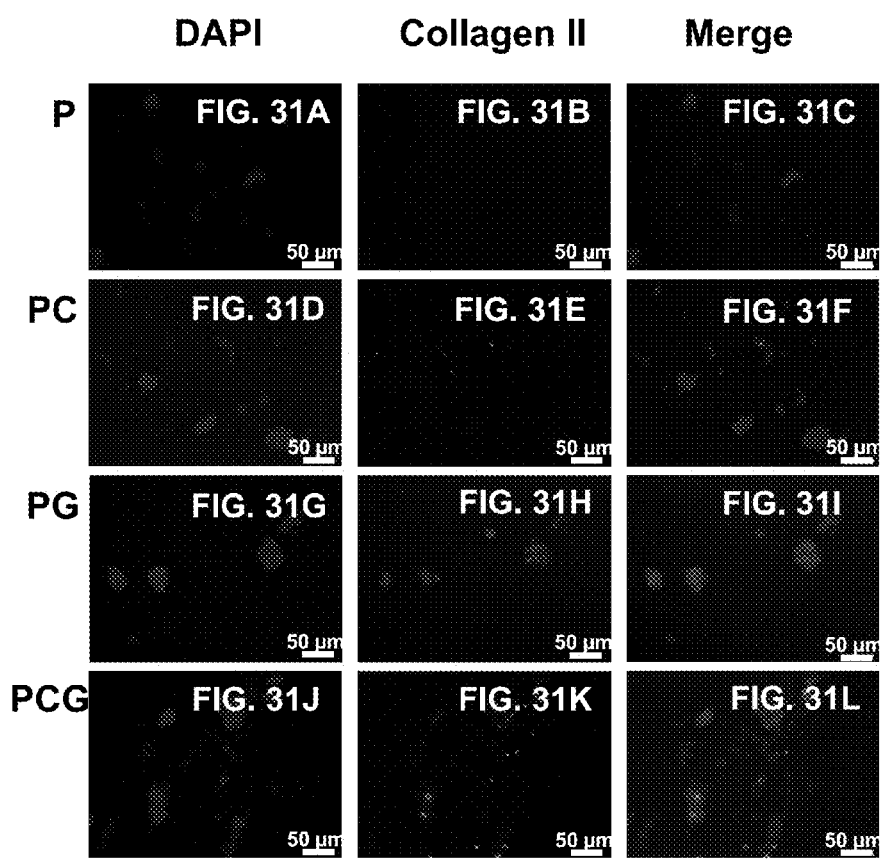
FIGS. 31A-31L demonstrate BM-MSCs cultured on P (FIGS. 31A-31C), PC (FIGS. 31D-31F), PG (FIGS. 31G-31I), or PCG (FIGS. 31J-31L) hydrogels without chondrogenic induction. After about 4 days in culture BM-MSCs were fixed and counter-stained with DAPI (FIGS. 31A, 31D, 31G, and 31I, blue), or Collagen II (FIGS. 31B, 31E, 31H, and 31Y, red) using a Collagen II antibody. The merged images are shown in FIGS. 31C, 31F, 31I, and 31L.
Figures 32A, 32B, 32C, 32D:
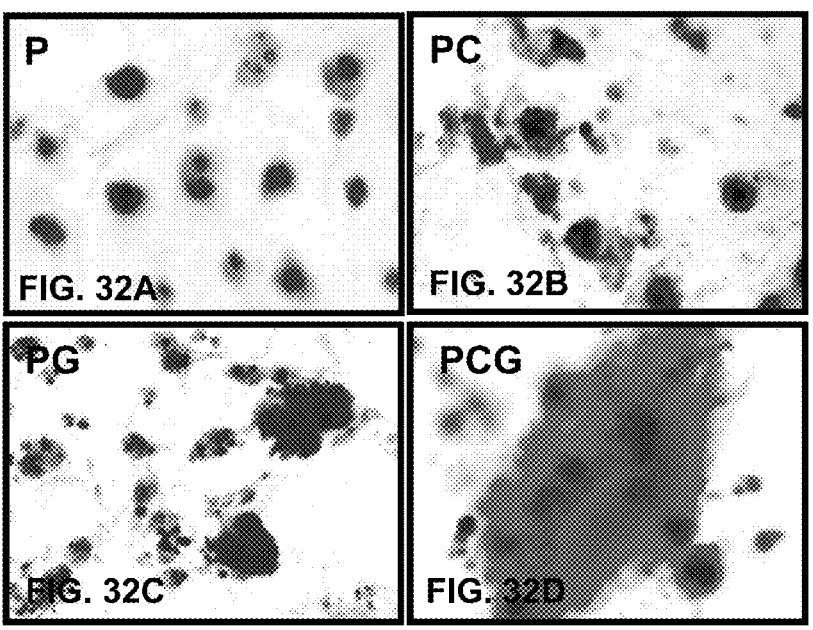
FIGS. 32A-32D demonstrate osteogenic differentiation of BM-MSCs grown on O (FIG. 32A), PC (FIG. 32B), PG (FIG. 32C), or PCG (FIG. 32D) hydrogels and visualized by Alizarin Red S staining after about 7 days of culture.

Chondrogenic Differentiation:

The effect of graphene on the chondrogenic differentiation of BM-MSC in 3D hydrogel was tested. The process of chondrogenic differentiation of BM-MSCs can involve condensation of progenitors, chondrocyte differentiation, and deposition of a cartilaginous extracellular matrix (ECM), resulting in the formation of cartilage during chondrogenesis. Chondrogenic differentiation was estimated by alcian blue staining of the glycosaminoglycans (GAGs) present in aggrecan, which forms the major component of cartilage ECM (FIGS. 27A-27D). As shown in FIGS. 27A-27D, BM-MSCs in PCG hydrogels produced larger cartilaginous nodules than the other hydrogels. PCG hydrogels also exhibited the most intense blue staining compared to P, PC, or PG hydrogel, which indicates that graphene induced more deposition of glycosaminoglycan and promoted chondrogenic differentiation. PG or PCG hydrogels showed significantly more alcian blue staining than P or PG hydrogels (FIG. 28). The immunofluorescence staining for collagen type II three days after induction of BM-MSCs on PC, PG, and PCG hydrogels showed significantly higher accumulation of collagen type II than in P hydrogels (FIGS. 29A-29L and 30). PCG hydrogels displayed the most intense staining of collagen type II. A similar trend was observed with BM-MSCs cultured on hydrogels without chondrogenic induction (FIGS. 31A-31L). These results suggest that BM-MSCs encapsulated inside the PCG hydrogel could produce more GAG and collagen type II than the other hydrogels. FIGS. 39A-39D demonstrate Alcian blue staining of hMSCs after about 14 days of culture on P (FIG. 39A), PC (FIG. 39B), PG (FIG. 39C), or PCG (FIG. 39D) hydrogels with chondrogenic differentiation.

Osteogenic Differentiation:

In this Example, the influence of graphene on the osteogenic differentiation of BM-MSCs in hydrogel was investigated by plating mouse BM-MSCs on hydrogels. The osteogenic differentiation of BM-MSCs was evidenced by the accumulation of calcium or increase of alkaline phosphatase, which is an early marker of osteogenesis. It was determined whether PCG hydrogels promoted the differentiation of BM-MSCs into cells with an osteoblast-like phenotype expressing the bone markers, osteopontin (OPN) and alkaline phosphatase (ALP). It was also determined whether PCG hydrogels demonstrated increased calcium mineralization.

After seven days of osteogenic induction, the extent of mineralization of BM-MSCs cultured on P, PC, PG and PCG hydrogel was assessed via alizarin red S staining of calcium (FIGS. 32A-32D). The extent of mineralization in MSCs cultured on PCG hydrogels was observed to be greater than that of MSCs cultured on P, PC or PG hydrogels.

Figure 33:
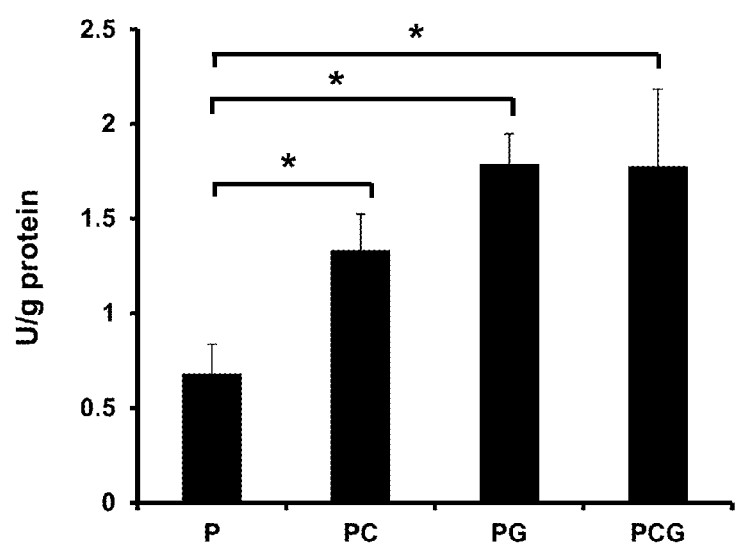
FIG. 33 is a graph demonstrating alkaline phosphatase (ALP) activity in BM-MSCs cultured on various hydrogels at day 7 after osteogenic differentiation. Results were normalized by grams of protein and presented in the amount of p-nitrophenol (mmol/mL/min/g/protein). Results are expressed as the average (standard deviation with n=3 for each bar).
Figures 34A, 34B, 34C, 34D, 34E, 34F, 34G, 34H, 34I, 34J, 34K, 34L:
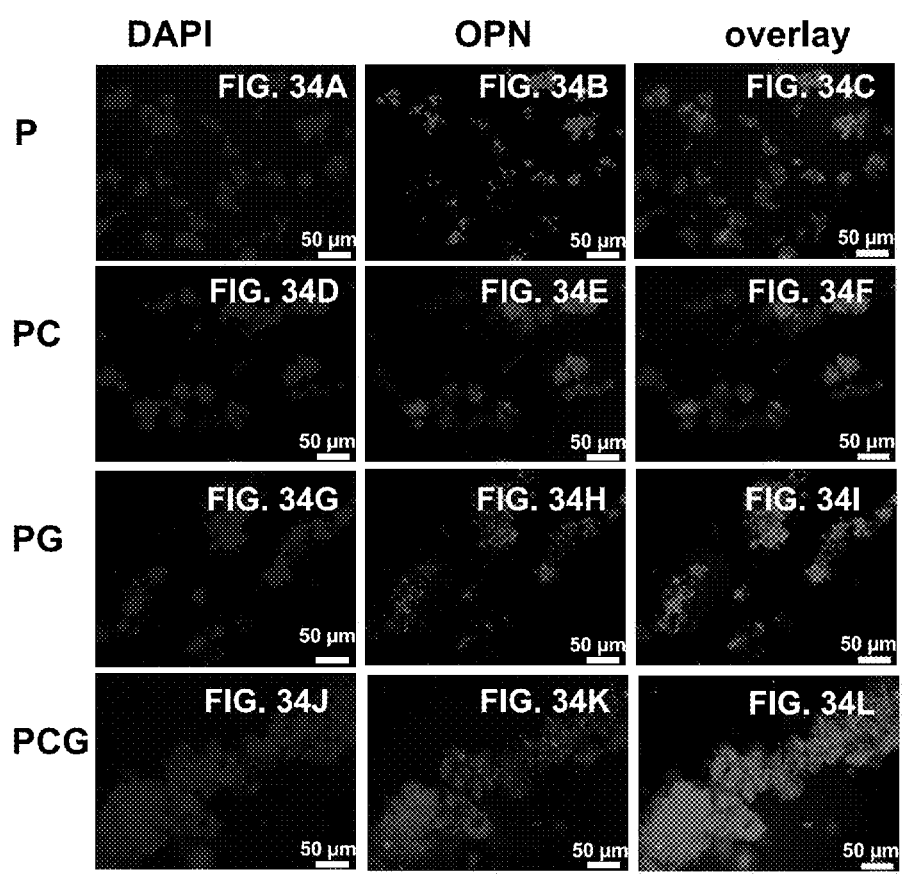
FIGS. 34A-34L demonstrate immunostaining of mouse BM-MSCs cultured on different hydrogels (P, FIGS. 34A-34C; PC, 34D-34F; PG, 34G-I; or PCG 34J-34L. After about 3 days in culture with osteogenic differentiation medium, cells were counter-stained with DAPI (blue) (FIGS. 34A, 34D, 34G, and 34J) and OPN using an OPN antibody (red)
Figure 35:
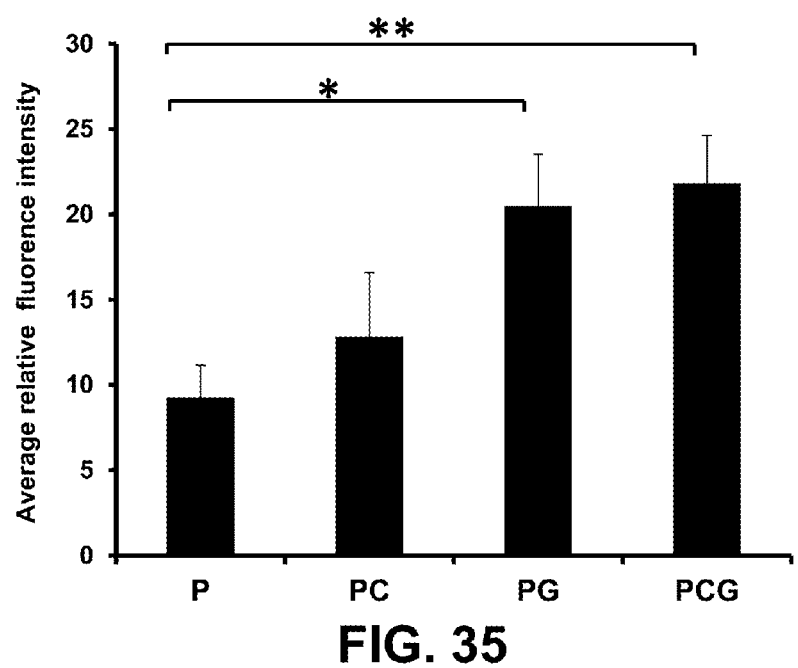
FIG. 35 shows a graph demonstrating quantification of OPN in the cells of FIGS. 34A-34L. The quantification of OPN by Image J was based on measuring the total integrity density of OPN red pixels, and then normalized to the total integrity density of DAPI blue pixels.

PCG hydrogel-grown cells were observed to have significantly greater levels of secreted ALP compared to P, PC, or PG hydrogels (FIG. 33). Immunostaining of OPN secreted by BM-MSCs cultured on the different hydrogels is shown in FIGS. 34A-34L. After three days of culture with osteogenic induction, OPN secreted by BM-MSCs cultured on PG or PCG hydrogel demonstrated significantly more intense fluorescence than on BM-MSCs cultured P hydrogel (FIG. 35). Without osteogenic induction, BM-MSCs on PG or PCG hydrogel secreted OPN but not on P or PG hydrogels (FIGS. 36A-36L). These results suggest that graphene in the hydrogel can enhance the osteogenic differentiation of BM-MSCs.

Figures 37A, 37B, 37C, 37D, 37E, 37F, 37G, 37H:
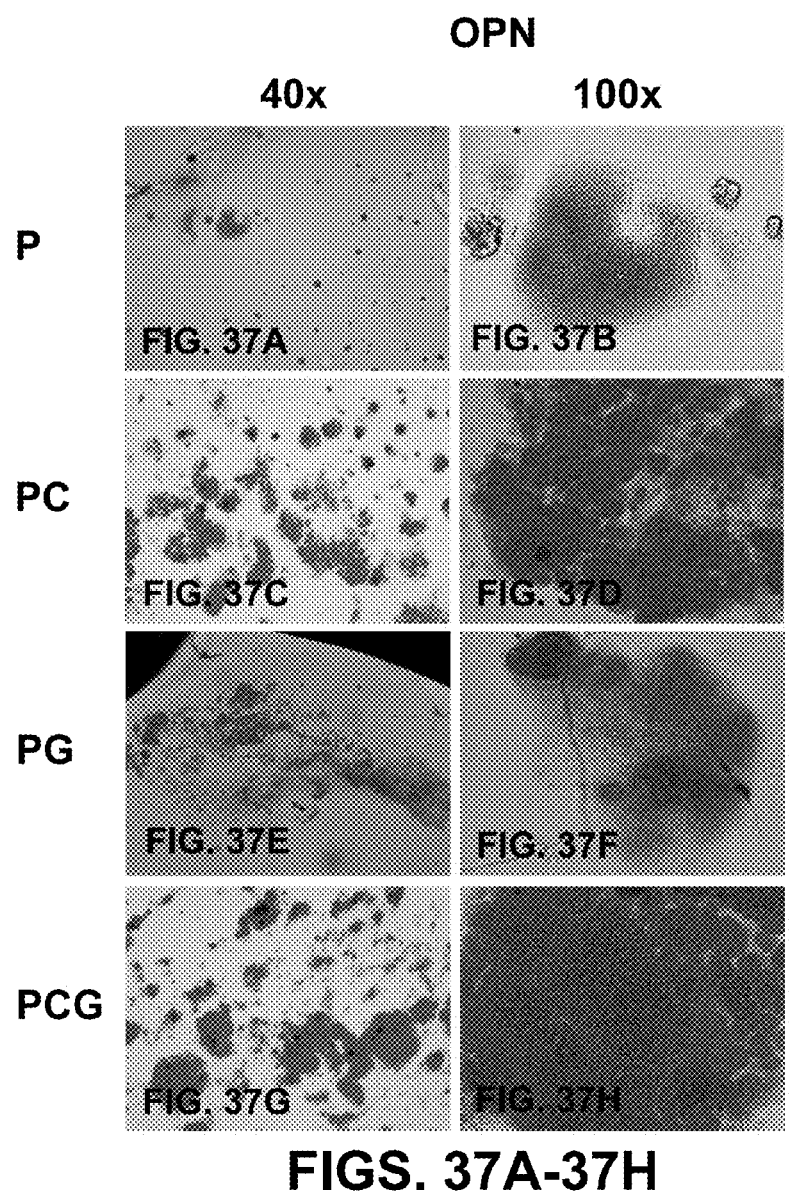
FIGS. 37A-37H demonstrate Alizarin Red S staining of hMSCs after about 7 days of incubation on different hydrogels (P, FIGS. 37A-37B; PC FIGS. 37C-37D; PG, 37E-37F; and PCG FIGS. 37G-37H) with osteogenic differentiation medium.
Figures 38A, 38B, 38C, 38D, 38E, 38F, 38G, 38H, 38I, 38J, 38K, 38L:
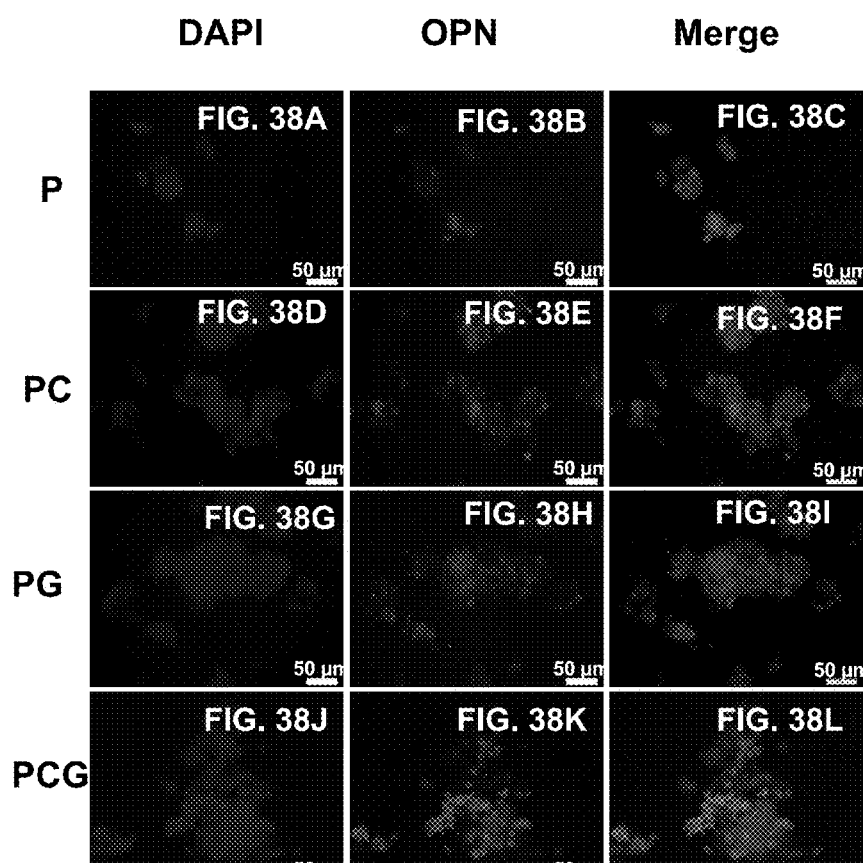
FIGS. 38A-38L demonstrate immunostaining of hMSCs cultured on P (FIGS. 38A-38C), PC (FIGS. 38D-38F), PG.
Figures 39A, 39B, 39C, 39D:
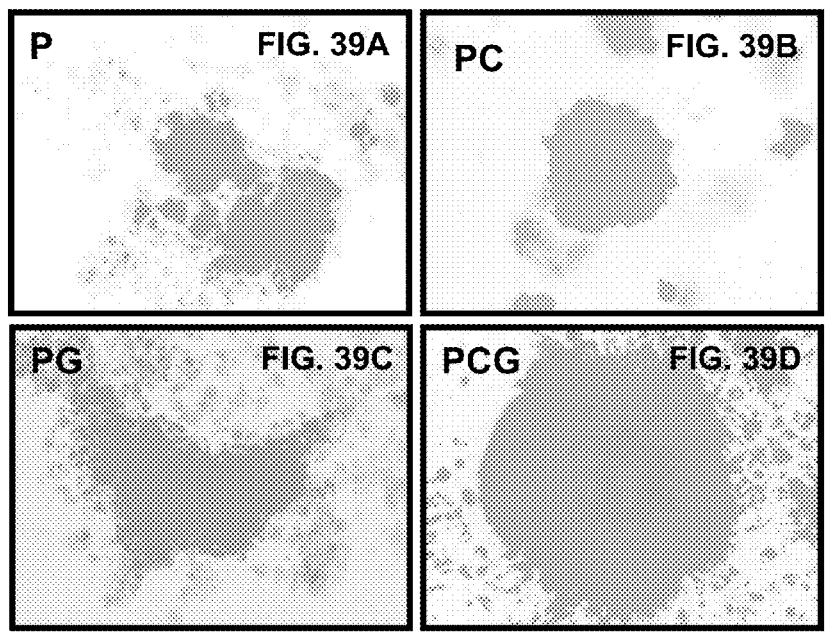
FIGS. 39A-39D demonstrate Alcian blue staining of hMSCs after about 14 days of culture on P (FIG. 39A), PC (FIG. 39B), PG (FIG. 39C), or PCG (FIG. 39D) hydrogels with chondrogenic differentiation.

FIGS. 37A-37H demonstrate Alizarin Red S staining of hMSCs after about 7 days of incubation on different hydrogels (P, FIGS. 37A-37B; PC FIGS. 37C-37D; PG, 37E-37F; and PCG FIGS. 37G-37H) with osteogenic differentiation medium. FIGS. 38A-38L demonstrate immunostaining of hMSCs cultured on P (FIGS. 38A-38C), PC (FIGS. 38D-38F), PG. (FIGS. 38G-38I) or PCG (FIGS. 38J-38L) hydrogels after about 7 days of treatment with osteogenic differentiation medium. After about 7 days of treatment, cells were stained with DAPI (blue) (FIGS. 38A, 38D, 38G, and 38J) or OPN antibody (red) (FIGS. 38B, 38E, 38H, and 38K). The merged images are shown in FIGS. 38C, 38F, 38I, and 38L.

Discussion

Overall, the results shown at least in this Example demonstrate that the PCG hydrogel can enhance the multipotent differentiation of MSCs, including BM-MSCs. It was previously reported that the differentiation of MSCs to adipocytes was greatly suppressed on 2D graphene membranes due to the denaturation of insulin, a key regulator of fatty acid biosynthesis, upon $\pi$-$\pi$ adsorption on graphene. However, electrostatic binding of insulin to graphene oxide does not interfere with adipogenesis. Here, graphene incorporated into a 3D hydrogel significantly enhanced adipogenic differentiation instead of inhibiting it as did 2D graphene. In the three dimensional PCG hydrogel, the insulin is not denatured because it is absorbed into the hydrogel and not directly onto the graphene sheets through $\pi$-$\pi$ interaction.

To confirm chondrogenesis of BM-MSCs in the hydrogel, alcian blue staining of GAG and immunostaining of the end-stage differentiation marker, collagen type II, were performed. The PCG hydrogel exhibited intense alcian blue staining and collagen type II immunostaining, showing that it enhanced the chondrogenesis of BM-MSCs. I was also demonstrated that the PCG hydrogel enhanced osteogenesis by alizarin red staining of calcium, alkaline phosphatase activity, and OPN immunostaining.

There are several properties of the PCG hydrogel that might be responsible for the enhancement of BM-MSC differentiation. The graphene sheet inside the hydrogel might behave similarly to RGD as graphene promoted adherence of mesenchymal stromal cells. The PCG hydrogel could also be acting as a preconcentration platform for inducers such as dexamethasone or ascorbic acid to accelerate MSCs growing on it toward the adipogenic, chrodrogenic, and osteogenic lineage. The BM-MSCs cultured on PCG hydrogel formed large spheroids, which might also account for the enhanced multipotent differentiation efficiency.

We claim:

1. A method comprising:
  contacting a cell with a hydrogel for a period of time, where the hydrogel comprises:
    at least two acrylated chitosan-graphene monomers, where each chitosan-graphene monomer comprises: carboxylic acid functionalized graphene, where the chitosan component of the chitosan-graphene monomer is covalently bonded to the carboxylic acid functionalized graphene component of the chitosan-graphene monomer; and
    polyethylene (glycol) diacrylate (PEGDA), where the (PEGDA) covalently crosslinks the at least two acrylated chitosan-graphene monomers.

2. The method of claim 1, further comprising the step of culturing the cell and the hydrogel in cell culture media.

3. The method of claim 2, where the cell culture media is a differentiation cell culture media.

4. The method of claim 3, wherein the differentiation cell culture media is an adipogenic cell culture media, osteogenic cell culture media, chondrogenic cell culture media, or combination thereof.

5. The method of claim 3, wherein the cell and hydrogel are cultured in the differentiation cell culture media for about 7 days.

6. The method of claim 1, wherein the cell is a stem cell.

7. The method of claim 6, wherein the stem cell is selected from the group consisting of: a pluripotent stem cell, a totipotent stem cell, a multipotent stem cell, an adult stem cell, and an induced pluripotent stem cell.

8. The method of claim 1, wherein the cell is a bone-marrow mesenchymal stem cell.

9. The method of claim 1, where the period of time ranges from about 1 hour to about 14 days.

10. The method of claim 1, wherein the cell proliferates to form a population of cells after the period of time.

11. The method of claim 10, wherein the population of cells is harvested by separating the population of cells from the hydrogel to form harvested cells.

12. The method of claim 11, wherein the harvested cells are delivered to a subject in need thereof.

13. The method of claim 12, wherein the cell is autologous, allogenic, xenogeneic, or syngeneic.

14. The method claim 1, wherein after the period of time the cell differentiates to form a differentiated population of cells.

15. The method of claim 14, wherein the differentiated population of cells contains at least one cell selected from the group consisting of: a chondrocyte, an adipocyte, and an osteocyte.

16. The method of claim 14, wherein the differentiated population of cells is harvested by separating the differentiated population of cells from the hydrogel.

17. The method of claim 16, wherein the cell is autologous, allogenic, xenogeneic, or syngeneic.

18. The method of claim 14, wherein the graphene enhances differentiation of the cell.

19. The method of claim 10, further comprising the step of delivering the hydrogel and the population of cells to a subject in need thereof.

20. The method of claim 14, further comprising the step of delivering the hydrogel and the differentiated population of cells to a subject in need thereof.

21. The method of claim 1, wherein the hydrogel further comprises N-Isopropylacrylamide (NIPAM), where the NIPAM is crosslinked at least one of the acrylated chitosan-graphenemonomers.

* * * * *